(12) United States Patent
Ek

(10) Patent No.: US 8,523,872 B2
(45) Date of Patent: Sep. 3, 2013

(54) TIBIAL RESURFACING SYSTEM

(75) Inventor: Steven Ek, Bolton, MA (US)

(73) Assignee: Arthrosurface Incorporated, Franklin, MA (US)

( * ) Notice: Subject to any disclaimer, the term of this patent is extended or adjusted under 35 U.S.C. 154(b) by 1139 days.

(21) Appl. No.: 11/623,513

(22) Filed: Jan. 16, 2007

(65) Prior Publication Data
US 2007/0118136 A1 May 24, 2007

Related U.S. Application Data

(62) Division of application No. 10/308,718, filed on Dec. 3, 2002, now Pat. No. 7,163,541.

(51) Int. Cl.
*A61B 17/56* (2006.01)

(52) U.S. Cl.
USPC .................................................. 606/96

(58) Field of Classification Search
USPC ..................................... 606/96–98
See application file for complete search history.

(56) References Cited

U.S. PATENT DOCUMENTS

| | | | |
|---|---|---|---|
| 992,819 A | 5/1911 | Springer |
| 1,451,610 A | 4/1923 | Gestas |
| 2,267,925 A | 12/1941 | Johnston |
| 2,379,984 A | 7/1943 | Nereaux |
| 2,381,102 A | 10/1943 | Boyd |
| 2,570,465 A | 10/1951 | Lundholm |
| 3,176,395 A | 4/1965 | Warner et al. |
| 3,715,763 A | 2/1973 | Link |
| 3,840,905 A | 10/1974 | Deane |

(Continued)

FOREIGN PATENT DOCUMENTS

| AU | 2001262308 | 12/2001 |
|---|---|---|
| AU | 2001259327 B2 | 2/2005 |

(Continued)

OTHER PUBLICATIONS

Notice of Allowance dated Jan. 5, 2011 issued in related U.S. Appl. No. 11/326,133.

(Continued)

*Primary Examiner* — Kevin T Truong
*Assistant Examiner* — Michael Araj
(74) *Attorney, Agent, or Firm* — Grossman Tucker Perreault & Pfleger PLLC

(57) ABSTRACT

A tibial resurfacing system is provided that includes a drill guide, bone chisel and implant. In one aspect, the system includes a drill guide that includes a targeting ring that is shaped to be placed on the superior tibial surface and a bore section that is connected to the ring to create an axis through the tibia to the superior tibial surface in the vicinity of the targeting ring. The drill guide permits a drill pin and/or drill to be advanced through the tibia to the superior tibial surface. In another aspect, a bone chisel is provided that includes an elongated tubular structure having a first end and a bone-cutting end, and the bone-cutting end is terminated in a transverse angle thereby creating an elliptical bone-cutting face. In another aspect, an implant is provided that includes an angled bearing element formed of a cylindrical member having a first end and a second end. The first end is formed at an angle that creates an elliptical face of the first end, and the first end defines a load-bearing surface of an articular surface.

4 Claims, 13 Drawing Sheets

(56) References Cited

U.S. PATENT DOCUMENTS

| | | |
|---|---|---|
| 3,852,830 A | 12/1974 | Marmor |
| 4,016,651 A | 4/1977 | Kawahara et al. |
| 4,016,874 A | 4/1977 | Maffei et al. |
| 4,034,418 A | 7/1977 | Jackson et al. |
| 4,044,464 A | 8/1977 | Schiess et al. |
| 4,158,894 A | 6/1979 | Worrell |
| 4,319,577 A | 3/1982 | Bofinger et al. |
| 4,330,891 A | 5/1982 | Brånemark et al. |
| 4,340,978 A | 7/1982 | Buechel et al. |
| 4,344,192 A | 8/1982 | Imbert |
| 4,433,687 A | 2/1984 | Burke et al. |
| 4,462,120 A | 7/1984 | Rambert et al. |
| 4,474,177 A | 10/1984 | Whiteside |
| 4,484,570 A | 11/1984 | Sutter et al. |
| 4,531,517 A | 7/1985 | Forte et al. |
| 4,535,768 A | 8/1985 | Hourahane et al. |
| 4,565,768 A | 1/1986 | Nonogaki et al. |
| 4,634,720 A | 1/1987 | Dorman et al. |
| 4,655,752 A | 4/1987 | Honkanen et al. |
| 4,661,536 A | 4/1987 | Dorman et al. |
| 4,662,371 A | 5/1987 | Whipple et al. |
| 4,664,669 A | 5/1987 | Ohyabu et al. |
| 4,673,407 A | 6/1987 | Martin |
| 4,693,986 A | 9/1987 | Vit et al. |
| 4,708,139 A | 11/1987 | Dunbar, IV |
| 4,712,545 A | 12/1987 | Honkanen |
| 4,714,478 A | 12/1987 | Fischer |
| 4,719,908 A | 1/1988 | Averill et al. |
| 4,722,331 A * | 2/1988 | Fox .................. 606/96 |
| 4,729,761 A | 3/1988 | White |
| 4,781,182 A | 11/1988 | Purnell et al. |
| 4,788,970 A | 12/1988 | Kara et al. |
| 4,823,780 A | 4/1989 | Odensten et al. |
| 4,842,604 A | 6/1989 | Dorman et al. |
| 4,896,663 A | 1/1990 | Vandewalls |
| 4,911,153 A | 3/1990 | Border |
| 4,911,720 A | 3/1990 | Collier |
| 4,920,958 A | 5/1990 | Walt et al. |
| 4,927,421 A | 5/1990 | Goble et al. |
| 4,938,778 A | 7/1990 | Ohyabu et al. |
| 4,940,467 A | 7/1990 | Tronzo |
| 4,945,904 A * | 8/1990 | Bolton et al. ............ 606/96 |
| 4,976,037 A | 12/1990 | Hines |
| 4,978,258 A | 12/1990 | Lins |
| 4,979,957 A | 12/1990 | Hodorek |
| 4,989,110 A | 1/1991 | Zevin et al. |
| 4,990,163 A | 2/1991 | Ducheyne et al. |
| 4,997,434 A | 3/1991 | Seedhom et al. |
| 4,998,938 A | 3/1991 | Ghajar et al. |
| 5,007,930 A | 4/1991 | Dorman et al. |
| 5,019,104 A | 5/1991 | Whiteside et al. |
| 5,053,049 A | 10/1991 | Campbell |
| 5,092,895 A | 3/1992 | Albrektsson et al. |
| 5,100,405 A | 3/1992 | McLaren |
| 5,127,920 A | 7/1992 | MacArthur |
| 5,154,720 A | 10/1992 | Trott et al. |
| 5,180,384 A | 1/1993 | Mikhail |
| 5,192,291 A | 3/1993 | Pannek, Jr. |
| 5,201,881 A | 4/1993 | Evans |
| 5,207,753 A | 5/1993 | Badrinath |
| 5,211,647 A | 5/1993 | Schmieding |
| 5,224,945 A | 7/1993 | Pannek, Jr. |
| 5,234,435 A | 8/1993 | Seagrave, Jr. |
| 5,255,838 A | 10/1993 | Gladdish, Jr. et al. |
| 5,263,498 A | 11/1993 | Caspari et al. |
| 5,263,987 A | 11/1993 | Shah |
| 5,282,863 A | 2/1994 | Burton |
| 5,290,313 A | 3/1994 | Heldreth |
| 5,312,411 A | 5/1994 | Steele |
| 5,314,478 A | 5/1994 | Oka et al. |
| 5,314,482 A | 5/1994 | Goodfellow et al. |
| 5,324,295 A | 6/1994 | Shapiro |
| 5,336,224 A | 8/1994 | Selman |
| 5,354,300 A | 10/1994 | Goble et al. |
| 5,358,525 A | 10/1994 | Fox et al. |
| 5,360,446 A | 11/1994 | Kennedy |
| 5,374,270 A | 12/1994 | McGuire et al. |
| 5,383,937 A | 1/1995 | Mikhail |
| 5,387,218 A | 2/1995 | Meswania |
| 5,395,401 A | 3/1995 | Bahler |
| 5,409,490 A | 4/1995 | Ethridge |
| 5,409,494 A | 4/1995 | Morgan |
| 5,413,608 A | 5/1995 | Keller |
| 5,423,822 A | 6/1995 | Hershberger |
| 5,423,823 A | 6/1995 | Schmieding |
| 5,458,643 A | 10/1995 | Oka et al. |
| 5,480,443 A | 1/1996 | Elias |
| 5,486,178 A | 1/1996 | Hodge |
| 5,509,918 A | 4/1996 | Romano |
| 5,520,695 A | 5/1996 | Luckman |
| 5,522,900 A | 6/1996 | Hollister |
| 5,534,031 A | 7/1996 | Matsuzaki et al. |
| 5,540,696 A | 7/1996 | Booth, Jr. et al. |
| 5,562,664 A | 10/1996 | Durlacher et al. |
| 5,580,353 A | 12/1996 | Mendes et al. |
| 5,591,170 A | 1/1997 | Spievack et al. |
| 5,593,450 A | 1/1997 | Scott et al. |
| 5,595,193 A | 1/1997 | Walus et al. |
| 5,597,273 A | 1/1997 | Hlrsch |
| 5,601,550 A | 2/1997 | Esser |
| 5,607,480 A | 3/1997 | Beaty |
| 5,616,146 A | 4/1997 | Murray |
| 5,620,055 A | 4/1997 | Javerlhac |
| 5,624,463 A | 4/1997 | Stone et al. |
| 5,632,745 A | 5/1997 | Schwartz |
| 5,634,927 A | 6/1997 | Houston et al. |
| 5,645,598 A | 7/1997 | Brosnahan, III |
| 5,681,311 A | 10/1997 | Foley et al. |
| 5,681,320 A | 10/1997 | McGuire |
| 5,682,886 A | 11/1997 | Delp et al. |
| 5,683,400 A | 11/1997 | McGuire |
| 5,683,465 A | 11/1997 | Shinn et al. |
| 5,683,466 A | 11/1997 | Viatle |
| 5,700,264 A | 12/1997 | Zucherman et al. |
| 5,700,265 A | 12/1997 | Romano |
| 5,702,401 A | 12/1997 | Shaffer |
| 5,702,465 A | 12/1997 | Burkinshaw |
| 5,702,467 A | 12/1997 | Gabriel et al. |
| 5,741,266 A | 4/1998 | Moran et al. |
| 5,765,973 A | 6/1998 | Hirsch et al. |
| 5,769,855 A | 6/1998 | Bertin et al. |
| 5,769,899 A | 6/1998 | Schwartz et al. |
| 5,771,310 A | 6/1998 | Vannah |
| 5,776,137 A | 7/1998 | Katz |
| 5,782,835 A | 7/1998 | Hart et al. |
| 5,800,440 A | 9/1998 | Stead |
| 5,810,851 A | 9/1998 | Yoon |
| 5,816,811 A | 10/1998 | Beaty |
| 5,817,095 A | 10/1998 | Smith |
| 5,824,087 A | 10/1998 | Aspden et al. |
| 5,824,105 A | 10/1998 | Ries et al. |
| RE36,020 E | 12/1998 | Moore et al. |
| 5,882,350 A | 3/1999 | Ralph et al. |
| 5,885,297 A | 3/1999 | Matsen, III |
| 5,885,298 A | 3/1999 | Herrington et al. |
| 5,888,210 A | 3/1999 | Draenert |
| 5,893,889 A | 4/1999 | Harrington |
| 5,895,390 A | 4/1999 | Moran et al. |
| 5,911,126 A | 6/1999 | Massen |
| 5,918,604 A | 7/1999 | Whelan |
| 5,919,196 A | 7/1999 | Bobic et al. |
| 5,928,239 A | 7/1999 | Mirza |
| 5,928,241 A | 7/1999 | Menut et al. |
| 5,928,286 A | 7/1999 | Ashby et al. |
| 5,964,752 A | 10/1999 | Stone |
| 5,964,768 A | 10/1999 | Huebner |
| 5,964,808 A | 10/1999 | Blaha et al. |
| 5,968,050 A | 10/1999 | Torrie |
| 5,989,269 A | 11/1999 | Vibe-Hansen et al. |
| 5,990,382 A | 11/1999 | Fox |
| 5,997,543 A | 12/1999 | Truscott |
| 5,997,582 A | 12/1999 | Weiss |
| 6,004,323 A | 12/1999 | Park et al. |
| 6,010,502 A | 1/2000 | Bagby |

| Patent | Kind | Date | Inventor |
|---|---|---|---|
| 6,015,411 | A | 1/2000 | Ohkoshi et al. |
| 6,017,348 | A | 1/2000 | Hart et al. |
| 6,019,767 | A | 2/2000 | Howell |
| 6,019,790 | A | 2/2000 | Holmberg et al. |
| 6,045,564 | A | 4/2000 | Walen |
| 6,052,909 | A | 4/2000 | Gardner |
| 6,059,831 | A | 5/2000 | Braslow |
| 6,071,310 | A | 6/2000 | Picha et al. |
| 6,081,741 | A | 6/2000 | Hollis |
| 6,086,593 | A | 7/2000 | Bonutti |
| 6,086,614 | A | 7/2000 | Mumme |
| 6,102,948 | A | 8/2000 | Brosnahan, III |
| 6,120,511 | A * | 9/2000 | Chan ............ 606/96 |
| 6,120,542 | A | 9/2000 | Camino et al. |
| 6,132,433 | A | 10/2000 | Whelan |
| 6,146,385 | A | 11/2000 | Torrie et al. |
| 6,149,654 | A | 11/2000 | Johnson |
| 6,152,960 | A | 11/2000 | Pappas |
| 6,159,216 | A | 12/2000 | Burkinshaw et al. |
| 6,165,223 | A | 12/2000 | Metzger et al. |
| 6,168,626 | B1 | 1/2001 | Hyon et al. |
| 6,171,340 | B1 | 1/2001 | McDowell |
| 6,193,724 | B1 | 2/2001 | Chan |
| 6,206,885 | B1 | 3/2001 | Ghahremani et al. |
| 6,206,926 | B1 | 3/2001 | Pappas |
| 6,217,549 | B1 | 4/2001 | Selmon et al. |
| 6,217,619 | B1 | 4/2001 | Keller |
| 6,251,143 | B1 | 6/2001 | Schwartz et al. |
| 6,254,605 | B1 * | 7/2001 | Howell ............ 606/96 |
| 6,270,347 | B1 | 8/2001 | Webster et al. |
| 6,280,474 | B1 | 8/2001 | Cassidy et al. |
| 6,299,645 | B1 | 10/2001 | Ogden |
| 6,299,648 | B1 | 10/2001 | Doubler et al. |
| 6,306,142 | B1 | 10/2001 | Johanson et al. |
| 6,315,798 | B1 | 11/2001 | Ashby et al. |
| 6,322,500 | B1 | 11/2001 | Sikora et al. |
| 6,328,752 | B1 | 12/2001 | Sjostrom et al. |
| 6,342,075 | B1 | 1/2002 | MacArthur |
| 6,358,251 | B1 | 3/2002 | Mirza |
| 6,358,253 | B1 | 3/2002 | Torrie et al. |
| 6,364,910 | B1 | 4/2002 | Shultz et al. |
| 6,375,658 | B1 | 4/2002 | Hangody et al. |
| 6,383,188 | B2 | 5/2002 | Kuslich |
| 6,415,516 | B1 | 7/2002 | Tirado et al. |
| 6,443,954 | B1 | 9/2002 | Bramlet et al. |
| 6,451,023 | B1 | 9/2002 | Salazar et al. |
| 6,461,373 | B2 | 10/2002 | Wyman et al. |
| 6,468,309 | B1 | 10/2002 | Lieberman |
| 6,478,801 | B1 | 11/2002 | Ralph et al. |
| 6,478,822 | B1 | 11/2002 | Leroux et al. |
| 6,482,210 | B1 | 11/2002 | Skiba et al. |
| 6,494,914 | B2 | 12/2002 | Brown |
| 6,520,964 | B2 | 2/2003 | Tallarida et al. |
| 6,527,754 | B1 | 3/2003 | Tallarida et al. |
| 6,530,956 | B1 | 3/2003 | Mansmann |
| 6,540,786 | B2 | 4/2003 | Chibrac et al. |
| 6,551,322 | B1 | 4/2003 | Lieberman |
| 6,554,866 | B1 | 4/2003 | Aicher et al. |
| 6,575,980 | B1 | 6/2003 | Robie et al. |
| 6,575,982 | B1 | 6/2003 | Bonutti |
| 6,585,666 | B2 | 7/2003 | Suh et al. |
| 6,591,581 | B2 | 7/2003 | Schmieding |
| 6,599,321 | B2 | 7/2003 | Hyde et al. |
| 6,602,258 | B1 | 8/2003 | Katz |
| 6,607,561 | B2 | 8/2003 | Brannon |
| 6,610,067 | B2 | 8/2003 | Tallarida |
| 6,610,095 | B1 | 8/2003 | Pope et al. |
| 6,623,474 | B1 | 9/2003 | Ponzi |
| 6,626,950 | B2 | 9/2003 | Brown et al. |
| 6,629,997 | B2 | 10/2003 | Mansmann |
| 6,632,246 | B1 | 10/2003 | Simon et al. |
| 6,679,917 | B2 | 1/2004 | Ek |
| 6,746,451 | B2 | 6/2004 | Middleton et al. |
| 6,755,837 | B2 | 6/2004 | Ebner |
| 6,755,865 | B2 | 6/2004 | Tarabishy |
| 6,783,550 | B2 | 8/2004 | MacArthur |
| 6,783,551 | B1 | 8/2004 | Metzger |
| 6,802,864 | B2 | 10/2004 | Tornier |
| 6,814,735 | B1 | 11/2004 | Zirngibl |
| 6,827,722 | B1 | 12/2004 | Schoenefeld |
| 6,860,902 | B2 | 3/2005 | Reiley |
| 6,884,246 | B1 | 4/2005 | Sonnabend et al. |
| 6,884,621 | B2 | 4/2005 | Liao et al. |
| 6,893,467 | B1 | 5/2005 | Bercovy |
| 6,923,813 | B2 | 8/2005 | Phillips et al. |
| 6,926,739 | B1 | 8/2005 | Oconnor |
| 6,962,577 | B2 | 11/2005 | Tallarida et al. |
| 6,969,393 | B2 | 11/2005 | Pinczewski et al. |
| 6,984,248 | B2 | 1/2006 | Hyde, Jr. |
| 6,989,016 | B2 | 1/2006 | Tallarida et al. |
| 7,029,479 | B2 | 4/2006 | Tallarida |
| 7,048,767 | B2 | 5/2006 | Namavar |
| 7,063,717 | B2 | 6/2006 | St. Pierre et al. |
| 7,112,205 | B2 | 9/2006 | Carrison |
| 7,115,131 | B2 | 10/2006 | Engh et al. |
| 7,118,578 | B2 | 10/2006 | West, Jr. et al. |
| 7,156,880 | B2 | 1/2007 | Evans et al. |
| 7,160,305 | B2 | 1/2007 | Schmieding |
| 7,163,541 | B2 | 1/2007 | Ek |
| 7,166,133 | B2 | 1/2007 | Evans et al. |
| 7,192,431 | B2 | 3/2007 | Hangody et al. |
| 7,192,432 | B2 | 3/2007 | Wetzler et al. |
| 7,204,839 | B2 | 4/2007 | Dreyfuss et al. |
| 7,204,854 | B2 | 4/2007 | Guederian et al. |
| 7,235,107 | B2 | 6/2007 | Evans et al. |
| 7,238,189 | B2 | 7/2007 | Schmieding et al. |
| 7,241,316 | B2 | 7/2007 | Evans et al. |
| 7,264,634 | B2 | 9/2007 | Schmieding |
| 7,290,347 | B2 | 11/2007 | Augustino et al. |
| 7,303,577 | B1 | 12/2007 | Dean |
| 7,311,702 | B2 | 12/2007 | Tallarida et al. |
| 7,361,195 | B2 | 4/2008 | Schwartz et al. |
| 7,371,260 | B2 | 5/2008 | Malinin |
| 7,462,199 | B2 | 12/2008 | Justin et al. |
| 7,468,075 | B2 | 12/2008 | Lang et al. |
| 7,476,250 | B1 | 1/2009 | Mansmann |
| 7,491,235 | B2 | 2/2009 | Fell |
| 7,501,073 | B2 | 3/2009 | Wen et al. |
| 7,510,558 | B2 | 3/2009 | Tallarida |
| 7,531,000 | B2 | 5/2009 | Hodorek |
| 7,559,932 | B2 | 7/2009 | Truckai et al. |
| 7,569,059 | B2 | 8/2009 | Cerundolo |
| 7,572,291 | B2 | 8/2009 | Gil et al. |
| 7,575,578 | B2 | 8/2009 | Wetzler et al. |
| 7,578,824 | B2 | 8/2009 | Justin et al. |
| 7,604,641 | B2 | 10/2009 | Tallarida et al. |
| 7,611,653 | B1 | 11/2009 | Elsner et al. |
| 7,618,451 | B2 | 11/2009 | Berez et al. |
| 7,618,462 | B2 | 11/2009 | Ek |
| 7,632,294 | B2 | 12/2009 | Milbodker et al. |
| 7,641,658 | B2 | 1/2010 | Shaolian et al. |
| 7,641,689 | B2 | 1/2010 | Fell et al. |
| 7,670,381 | B2 | 3/2010 | Schwartz |
| 7,678,151 | B2 | 3/2010 | Ek |
| 7,682,540 | B2 | 3/2010 | Boyan et al. |
| 7,687,462 | B2 | 3/2010 | Ting et al. |
| 7,708,741 | B1 | 5/2010 | Bonutti |
| 7,713,305 | B2 | 5/2010 | Ek |
| 7,722,676 | B2 | 5/2010 | Hanson et al. |
| 7,731,720 | B2 | 6/2010 | Sand et al. |
| 7,758,643 | B2 | 7/2010 | Stone et al. |
| 7,806,872 | B2 | 10/2010 | Ponzi |
| 7,815,645 | B2 | 10/2010 | Haines |
| 7,828,853 | B2 | 11/2010 | Ek et al. |
| 7,842,042 | B2 | 11/2010 | Reay-Young et al. |
| 7,857,817 | B2 | 12/2010 | Tallarida et al. |
| 7,896,883 | B2 | 3/2011 | Ek et al. |
| 7,896,885 | B2 | 3/2011 | Miniaci et al. |
| 7,901,408 | B2 | 3/2011 | Ek et al. |
| 7,914,545 | B2 | 3/2011 | Ek |
| 7,931,683 | B2 | 4/2011 | Weber et al. |
| 7,951,163 | B2 | 5/2011 | Ek |
| 7,955,382 | B2 | 6/2011 | Flanagan et al. |
| 7,959,636 | B2 | 6/2011 | Schmieding |
| 7,967,823 | B2 | 6/2011 | Ammann et al. |
| 7,993,360 | B2 | 8/2011 | Hacker et al. |
| 7,993,369 | B2 | 8/2011 | Dreyfuss |
| 7,998,206 | B2 | 8/2011 | Shepard |

| | | | | | | |
|---|---|---|---|---|---|---|
| 8,012,206 B2 | 9/2011 | Schmieding | | 2002/0156480 A1 | 10/2002 | Overes et al. |
| 8,021,367 B2 | 9/2011 | Bourke et al. | | 2002/0173797 A1 | 11/2002 | Van Zile et al. |
| 8,038,652 B2 | 10/2011 | Morrison et al. | | 2003/0028196 A1 | 2/2003 | Bonutti |
| 8,038,678 B2 | 10/2011 | Schmieding et al. | | 2003/0060887 A1 | 3/2003 | Ek |
| 8,043,315 B2 | 10/2011 | Shepard | | 2003/0065391 A1 | 4/2003 | Re et al. |
| 8,043,319 B2 | 10/2011 | Lyon et al. | | 2003/0100953 A1 | 5/2003 | Rosa et al. |
| 8,048,079 B2 | 11/2011 | Iannarone | | 2003/0105465 A1 | 6/2003 | Schmieding et al. |
| 8,048,157 B2 | 11/2011 | Albertorio | | 2003/0120276 A1 | 6/2003 | Tallarida et al. |
| 8,057,478 B2 | 11/2011 | Kuczynski et al. | | 2003/0120278 A1 | 6/2003 | Morgan et al. |
| 8,062,301 B2 | 11/2011 | Ammann et al. | | 2003/0130741 A1 | 7/2003 | McMinn |
| 8,062,319 B2 | 11/2011 | O'Quinn et al. | | 2003/0144736 A1 | 7/2003 | Sennett |
| 8,083,746 B2 | 12/2011 | Novak | | 2003/0171756 A1 | 9/2003 | Fallin et al. |
| 8,083,749 B2 | 12/2011 | Taber | | 2003/0181878 A1 | 9/2003 | Tallarida et al. |
| 8,083,803 B2 | 12/2011 | Albertorio et al. | | 2003/0195470 A1 | 10/2003 | Ponzi |
| 8,097,040 B2 | 1/2012 | Russo et al. | | 2003/0204195 A1 | 10/2003 | Keane et al. |
| 8,137,406 B2 | 3/2012 | Novak et al. | | 2003/0204267 A1 | 10/2003 | Hazebrouck et al. |
| 8,142,502 B2 | 3/2012 | Stone et al. | | 2003/0216669 A1 | 11/2003 | Lang et al. |
| 8,147,559 B2 | 4/2012 | Tallarida et al. | | 2003/0216742 A1 | 11/2003 | Wetzler et al. |
| 8,152,847 B2 | 4/2012 | Strzepa et al. | | 2003/0225456 A1 | 12/2003 | Ek |
| 8,162,947 B2 | 4/2012 | Dreyfuss | | 2003/0225457 A1 | 12/2003 | Justin et al. |
| 8,167,951 B2 | 5/2012 | Ammann et al. | | 2003/0229352 A1 | 12/2003 | Penenberg |
| 8,177,738 B2 | 5/2012 | Schmieding et al. | | 2004/0015170 A1 | 1/2004 | Tallarida et al. |
| 8,177,841 B2 | 5/2012 | Ek | | 2004/0033212 A1 | 2/2004 | Thomson et al. |
| 8,182,489 B2 | 5/2012 | Horacek | | 2004/0034359 A1 | 2/2004 | Schmieding et al. |
| 8,202,282 B2 | 6/2012 | Schmieding et al. | | 2004/0034437 A1 | 2/2004 | Schmieding |
| 8,202,296 B2 | 6/2012 | Burkhart | | 2004/0039389 A1 | 2/2004 | West, Jr. et al. |
| 8,202,297 B2 | 6/2012 | Burkhart | | 2004/0082906 A1 | 4/2004 | Tallarida et al. |
| 8,202,298 B2 | 6/2012 | Cook et al. | | 2004/0092946 A1 | 5/2004 | Bagga et al. |
| 8,202,306 B2 | 6/2012 | Dreyfuss | | 2004/0106928 A1 | 6/2004 | Ek |
| 8,202,318 B2 | 6/2012 | Willobee | | 2004/0133276 A1 | 7/2004 | Lang et al. |
| 8,211,112 B2 | 7/2012 | Novak et al. | | 2004/0138754 A1 | 7/2004 | Lang et al. |
| 8,221,455 B2 | 7/2012 | Shurnas et al. | | 2004/0138758 A1 | 7/2004 | Evans et al. |
| 8,231,653 B2 | 7/2012 | Dreyfuss | | 2004/0148030 A1 | 7/2004 | Ek |
| 8,231,674 B2 | 7/2012 | Albertorio et al. | | 2004/0153087 A1 | 8/2004 | Sanford et al. |
| 8,236,000 B2 | 8/2012 | Ammann et al. | | 2004/0167632 A1 | 8/2004 | Wen et al. |
| 8,298,247 B2 | 10/2012 | Sterrett et al. | | 2004/0167633 A1 | 8/2004 | Wen et al. |
| 8,298,284 B2 | 10/2012 | Cassani | | 2004/0176775 A1 | 9/2004 | Burkus et al. |
| 8,308,662 B2 | 11/2012 | Lo | | 2004/0193172 A1 | 9/2004 | Ross et al. |
| 8,308,732 B2 | 11/2012 | Millett et al. | | 2004/0193267 A1 | 9/2004 | Jones et al. |
| 8,323,347 B2 | 12/2012 | Guederian et al. | | 2004/0193268 A1 | 9/2004 | Hazebrouck |
| 8,328,716 B2 | 12/2012 | Schmieding et al. | | 2004/0193281 A1 | 9/2004 | Grimes |
| 8,333,774 B2 | 12/2012 | Morrison | | 2004/0199166 A1 | 10/2004 | Schmieding et al. |
| 8,343,186 B2 | 1/2013 | Dreyfuss et al. | | 2004/0204760 A1 | 10/2004 | Fitz et al. |
| 8,348,960 B2 | 1/2013 | Michel et al. | | 2004/0210309 A1 | 10/2004 | Denzer et al. |
| 8,348,975 B2 | 1/2013 | Dreyfuss | | 2004/0220574 A1 | 11/2004 | Pelo et al. |
| 8,353,915 B2 | 1/2013 | Helenbolt et al. | | 2004/0230315 A1 | 11/2004 | Ek |
| 8,361,159 B2 | 1/2013 | Ek | | 2004/0260303 A1 | 12/2004 | Carrison |
| 8,377,068 B2 | 2/2013 | Aker et al. | | 2005/0015153 A1 | 1/2005 | Gobel et al. |
| 8,382,789 B2 | 2/2013 | Weber et al. | | 2005/0038520 A1 | 2/2005 | Binette et al. |
| 8,382,810 B2 | 2/2013 | Peterson et al. | | 2005/0043805 A1 | 2/2005 | Chudik |
| 8,388,624 B2 | 3/2013 | Ek et al. | | 2005/0065612 A1 | 3/2005 | Winslow |
| 8,398,678 B2 | 3/2013 | Baker et al. | | 2005/0075642 A1 | 4/2005 | Felt |
| 8,409,209 B2 | 4/2013 | Ammann et al. | | 2005/0143731 A1 | 6/2005 | Justin et al. |
| 8,409,250 B2 | 4/2013 | Schmieding et al. | | 2005/0143745 A1 | 6/2005 | Hodorek et al. |
| 8,419,794 B2 | 4/2013 | ElAttrache et al. | | 2005/0143831 A1 | 6/2005 | Justin et al. |
| 8,425,554 B2 | 4/2013 | Denove et al. | | 2005/0149044 A1 | 7/2005 | Justin et al. |
| 8,430,909 B2 | 4/2013 | Dreyfuss | | 2005/0154398 A1 | 7/2005 | Miniaci et al. |
| 8,435,272 B2 | 5/2013 | Dougherty et al. | | 2005/0177171 A1 | 8/2005 | Wetzler et al. |
| 8,439,976 B2 | 5/2013 | Albertorio et al. | | 2005/0209705 A1 | 9/2005 | Niederauer et al. |
| 8,444,680 B2 | 5/2013 | Dooney, Jr. et al. | | 2005/0222687 A1 | 10/2005 | Vunjak-Novakovic et al. |
| 8,460,317 B2 | 6/2013 | Merves | | 2005/0229323 A1 | 10/2005 | Mills et al. |
| 8,460,318 B2 | 6/2013 | Murray et al. | | 2005/0251268 A1 | 11/2005 | Truncale |
| 8,460,350 B2 | 6/2013 | Albertorio et al. | | 2005/0287187 A1 | 12/2005 | Mansmann |
| 8,460,379 B2 | 6/2013 | Albertorio et al. | | 2006/0004461 A1 | 1/2006 | Justin et al. |
| 2001/0010023 A1 | 7/2001 | Schwartz et al. | | 2006/0009774 A1 | 1/2006 | Goble et al. |
| 2001/0012967 A1 | 8/2001 | Mosseri | | 2006/0052878 A1 | 3/2006 | Schmieding |
| 2001/0034526 A1 | 10/2001 | Kuslich et al. | | 2006/0058744 A1 | 3/2006 | Tallarida et al. |
| 2001/0039455 A1 | 11/2001 | Simon et al. | | 2006/0058809 A1 | 3/2006 | Zink et al. |
| 2001/0053914 A1 | 12/2001 | Landry et al. | | 2006/0058883 A1 | 3/2006 | Aram et al. |
| 2001/0056266 A1 | 12/2001 | Tallarida et al. | | 2006/0069394 A1 | 3/2006 | Weiler et al. |
| 2002/0022847 A1 | 2/2002 | Ray, III et al. | | 2006/0074430 A1 | 4/2006 | Deffenbaugh et al. |
| 2002/0022889 A1 | 2/2002 | Chibrac et al. | | 2006/0085077 A1 | 4/2006 | Cook et al. |
| 2002/0049444 A1 | 4/2002 | Knox | | 2006/0149370 A1 | 7/2006 | Schmieding et al. |
| 2002/0055783 A1 | 5/2002 | Tallarida et al. | | 2006/0167560 A1 | 7/2006 | Heck et al. |
| 2002/0106393 A1 | 8/2002 | Bianchi et al. | | 2006/0184187 A1 | 8/2006 | Surti |
| 2002/0138150 A1 | 9/2002 | Leclercq | | 2006/0195112 A1 | 8/2006 | Ek |
| 2002/0143342 A1 | 10/2002 | Hangody et al. | | 2006/0229726 A1 | 10/2006 | Ek |
| 2002/0147498 A1 | 10/2002 | Tallarida et al. | | 2006/0271059 A1 | 11/2006 | Reay-Young et al. |
| 2002/0155144 A1 | 10/2002 | Troczynski et al. | | 2007/0038302 A1 | 2/2007 | Shultz et al. |

| | | |
|---|---|---|
| 2007/0038307 A1 | 2/2007 | Webster et al. |
| 2007/0073394 A1 | 3/2007 | Seedhom et al. |
| 2007/0093842 A1 | 4/2007 | Schmieding |
| 2007/0093848 A1 | 4/2007 | Harris et al. |
| 2007/0093890 A1 | 4/2007 | Eliasen et al. |
| 2007/0093896 A1 | 4/2007 | Malinin |
| 2007/0118224 A1 | 5/2007 | Shah et al. |
| 2007/0134291 A1 | 6/2007 | Ting et al. |
| 2007/0233128 A1 | 10/2007 | Schmieding et al. |
| 2007/0244484 A1 | 10/2007 | Luginbuehl |
| 2007/0250067 A1 | 10/2007 | Schmieding et al. |
| 2007/0255399 A1 | 11/2007 | Eliasen et al. |
| 2007/0255412 A1 | 11/2007 | Hajaj et al. |
| 2007/0265700 A1 | 11/2007 | Eliasen et al. |
| 2007/0270873 A1 | 11/2007 | Flickinger et al. |
| 2007/0282455 A1 | 12/2007 | Luginbuehl et al. |
| 2007/0288031 A1 | 12/2007 | Dreyfuss et al. |
| 2007/0299519 A1 | 12/2007 | Schmieding |
| 2008/0004659 A1 | 1/2008 | Burkhart et al. |
| 2008/0015709 A1 | 1/2008 | Evans et al. |
| 2008/0027430 A1 | 1/2008 | Montgomery et al. |
| 2008/0033443 A1 | 2/2008 | Sikora et al. |
| 2008/0033447 A1 | 2/2008 | Sand |
| 2008/0039852 A1 | 2/2008 | Schmieding et al. |
| 2008/0046084 A1 | 2/2008 | Sledge |
| 2008/0086139 A1 | 4/2008 | Bourke et al. |
| 2008/0097618 A1 | 4/2008 | Baker et al. |
| 2008/0103506 A1 | 5/2008 | Volpi et al. |
| 2008/0154271 A1 | 6/2008 | Berberich et al. |
| 2008/0172125 A1 | 7/2008 | Ek |
| 2008/0183290 A1 | 7/2008 | Baird et al. |
| 2008/0188935 A1 | 8/2008 | Saylor et al. |
| 2008/0195113 A1 | 8/2008 | Sikora |
| 2008/0208201 A1 | 8/2008 | Moindreau et al. |
| 2008/0275512 A1 | 11/2008 | Albertirio et al. |
| 2008/0306483 A1 | 12/2008 | Iannarone |
| 2008/0317807 A1 | 12/2008 | Lu et al. |
| 2009/0018543 A1 | 1/2009 | Ammann et al. |
| 2009/0054899 A1 | 2/2009 | Ammann et al. |
| 2009/0069816 A1 | 3/2009 | Sasing et al. |
| 2009/0076512 A1 | 3/2009 | Ammann et al. |
| 2009/0112211 A1 | 4/2009 | Johnstone |
| 2009/0138077 A1 | 5/2009 | Weber et al. |
| 2009/0143783 A1 | 6/2009 | Dower |
| 2009/0143784 A1 | 6/2009 | Petersen et al. |
| 2009/0149860 A1 | 6/2009 | Scribner et al. |
| 2009/0198288 A1 | 8/2009 | Hoof et al. |
| 2009/0210057 A1 | 8/2009 | Liao et al. |
| 2009/0216285 A1 | 8/2009 | Ek et al. |
| 2009/0222012 A1 | 9/2009 | Karnes et al. |
| 2009/0228105 A1 | 9/2009 | Son et al. |
| 2009/0234452 A1 | 9/2009 | Steiner et al. |
| 2009/0264889 A1 | 10/2009 | Long et al. |
| 2009/0264928 A1 | 10/2009 | Blain |
| 2010/0003638 A1 | 1/2010 | Collins et al. |
| 2010/0015244 A1 | 1/2010 | Jain et al. |
| 2010/0028387 A1 | 2/2010 | Balasundaram et al. |
| 2010/0028999 A1 | 2/2010 | Nain |
| 2010/0036381 A1 | 2/2010 | Vanleeuwen et al. |
| 2010/0092535 A1 | 4/2010 | Cook et al. |
| 2010/0112519 A1 | 5/2010 | Hall et al. |
| 2010/0249930 A1 | 9/2010 | Myers |
| 2010/0256645 A1 | 10/2010 | Zajac et al. |
| 2010/0256758 A1 | 10/2010 | Gordon et al. |
| 2010/0268227 A1 | 10/2010 | Tong et al. |
| 2010/0268346 A1 | 10/2010 | Tong et al. |
| 2011/0009964 A1 | 1/2011 | Schwartz et al. |
| 2011/0059312 A1 | 3/2011 | Howling et al. |
| 2011/0066242 A1 | 3/2011 | Lu et al. |
| 2011/0125263 A1 | 5/2011 | Webster et al. |
| 2011/0152869 A1 | 6/2011 | Ek et al. |
| 2011/0196367 A1 | 8/2011 | Gallo |
| 2011/0238069 A1 | 9/2011 | Zajac et al. |
| 2011/0251621 A1 | 10/2011 | Sluss et al. |
| 2011/0257753 A1 | 10/2011 | Gordon et al. |
| 2011/0300186 A1 | 12/2011 | Hellstrom et al. |
| 2011/0301716 A1 | 12/2011 | Sirivisoot et al. |
| 2012/0027837 A1 | 2/2012 | DeMuth et al. |
| 2012/0109136 A1 | 5/2012 | Bourque et al. |
| 2012/0116502 A1 | 5/2012 | Su et al. |
| 2012/0123474 A1 | 5/2012 | Zajac et al. |
| 2012/0123541 A1 | 5/2012 | Albertorio et al. |
| 2012/0150225 A1 | 6/2012 | Burkart et al. |
| 2012/0150286 A1 | 6/2012 | Weber et al. |
| 2012/0165868 A1 | 6/2012 | Burkhart et al. |
| 2012/0183799 A1 | 7/2012 | Steele et al. |
| 2012/0185058 A1 | 7/2012 | Albertorio et al. |
| 2012/0189833 A1 | 7/2012 | Suchanek et al. |
| 2012/0189844 A1 | 7/2012 | Jain et al. |
| 2012/0209278 A1 | 8/2012 | Ries et al. |
| 2012/0265298 A1 | 10/2012 | Schmieding et al. |
| 2013/0023907 A1 | 1/2013 | Sterrett et al. |
| 2013/0023927 A1 | 1/2013 | Cassani |
| 2013/0046312 A1 | 2/2013 | Millett et al. |
| 2013/0096563 A1 | 4/2013 | Meade et al. |
| 2013/0096612 A1 | 4/2013 | Zajac et al. |
| 2013/0103104 A1 | 4/2013 | Krupp et al. |
| 2013/0110165 A1 | 5/2013 | Burkhart et al. |
| 2013/0138108 A1 | 5/2013 | Dryfuss et al. |
| 2013/0138150 A1 | 5/2013 | Baker et al. |
| 2013/0150885 A1 | 6/2013 | Dreyfuss |
| 2013/0165954 A1 | 6/2013 | Dreyfuss et al. |
| 2013/0165972 A1 | 6/2013 | Sullivan |
| 2013/0178871 | 7/2013 | Koogle, Jr. et al. |

FOREIGN PATENT DOCUMENTS

| | | |
|---|---|---|
| AU | 2002248198 B2 | 5/2007 |
| AU | 2005202099 B2 | 6/2007 |
| AU | 2002357284 B2 | 8/2007 |
| AU | 2006202337 B2 | 5/2008 |
| AU | 2003262428 | 8/2009 |
| AU | 2007216648 B2 | 11/2009 |
| AU | 2004216106 B2 | 6/2010 |
| AU | 2008207536 B2 | 3/2011 |
| CA | 2470194 C | 2/2011 |
| DE | 2933174 | 4/1980 |
| DE | 3516743 | 11/1986 |
| DE | 3840466 | 6/1990 |
| DE | 19505083 | 11/1995 |
| EP | 0241240 | 10/1987 |
| EP | 0350780 | 7/1989 |
| EP | 0350780 | 1/1990 |
| EP | 0485678 | 5/1992 |
| EP | 0327387 | 9/1992 |
| EP | 0505634 | 9/1992 |
| EP | 0736292 | 10/1996 |
| EP | 0903125 | 3/1999 |
| EP | 0903127 | 3/1999 |
| EP | 0993812 | 4/2000 |
| EP | 0661023 | 8/2001 |
| EP | 1426013 | 9/2004 |
| EP | 1278460 | 4/2009 |
| EP | 2314257 | 2/2013 |
| FR | 2242068 | 3/1975 |
| FR | 2642301 | 3/1990 |
| FR | 2676917 | 12/1992 |
| FR | 2693650 | 1/1994 |
| FR | 2718014 | 10/1995 |
| FR | 2733904 | 11/1996 |
| FR | 2739151 | 3/1997 |
| GB | 2281577 | 3/1995 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2001525210 | 12/2001 |
| JP | 2002291779 | 10/2002 |
| JP | 2003534096 | 11/2003 |
| WO | 8803781 | 6/1988 |
| WO | 8909578 | 10/1989 |
| WO | 9427507 | 12/1994 |
| WO | 9624304 | 8/1996 |
| WO | 9722306 | 6/1997 |
| WO | 0013597 | 3/2000 |

| | | |
|---|---|---|
| WO | 0105336 | 1/2001 |
| WO | 0166021 | 9/2001 |
| WO | 0166022 | 9/2001 |
| WO | 0182677 | 11/2001 |
| WO | 0191648 | 12/2001 |
| WO | 0191672 | 12/2001 |
| WO | 0217821 | 3/2002 |
| WO | 02086180 | 10/2002 |
| WO | 03047470 | 6/2003 |
| WO | 03051210 | 6/2003 |
| WO | 03051211 | 6/2003 |
| WO | 03061516 | 7/2003 |
| WO | 03065909 | 8/2003 |
| WO | 2004014261 | 2/2004 |
| WO | 2004026170 | 4/2004 |
| WO | 2004052216 | 6/2004 |
| WO | 2004075777 | 9/2004 |
| WO | 2005051231 | 6/2005 |
| WO | 2006004885 | 1/2006 |
| WO | 2006091686 | 8/2006 |

OTHER PUBLICATIONS

Supplemental Notice of Allowance dated Jan. 5, 2011 issued in related U.S. Appl. No. 11/326,133.
Canadian Office Action dated Jan. 7, 2011 issued in related Canadian Patent Application No. 2407440.
European Office Action dated Dec. 23, 2010 issued in related European Patent Application No. 028051882.9-2310.
European Office Action dated Dec. 30, 2010 issued in related European Patent Application No. 01997077.1-2310.
Supplemental Notice of Allowance dated Nov. 25, 2009 issued in related U.S. Appl. No. 10/373,463.
Office Action dated Dec. 24, 2009 issued in related U.S. Appl. No. 10/994,453.
Notice of Allowance dated Nov. 26, 2010 issued in related U.S. Appl. No. 11/209,170.
Supplemental Notice of Allowance dated Dec. 8, 2010 issued in related U.S. Appl. No. 11/209,170.
Notice of Allowance dated Dec. 13, 2010 issued in related U.S. Appl. No. 12/397,095.
USPTO Office Action dated Dec. 21, 2007 issued in corresponding U.S. Appl. No. 11/169,326.
USPTO Office Action dated Dec. 26, 2007 issued in U.S. Appl. No. 11/379,151.
USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.
USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.
USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office action dated May 10, 2006 issued in corresponding U.S. Appl. No. 10,373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.
USPTO Notice of Allowance issued Sep. 26, 2003 in U.S. Appl. No. 10/162,533.
USPTO Notice of Allowance issued May 12, 2003 in U.S. Appl. No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patnet application No. 2005202099.
AU Examiners report dated Jan. 12, 2007 issued in corresponding Australian patnet application No. 2006202337.
AU Examiners report dated Feb. 21, 2007 issued in corresponding Australian patnet application No. 2005202099.
AU Examiners report dated May 23, 2007 issued in corresponding Australian patnet application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.
EPO supplementary search report dated Aug. 30, 2004 issued in corresponding European application 01932833.5.
EPO Office Action dated Aug. 23, 2004, received in related EPO application No. 03 026 286.9 (4 pgs).
EPO Office Action dated Mar. 15, 2005, received in related EPO application No. 03 026 286.9, (3 pgs).
EPO Search Report received in related EPO Application No. 03 02 6286.9 dated Feb. 26, 2004 (5pgs).
EPO Search Report received in related EPO Application No. 03 02 6286.9 dated Apr. 27, 2004 (6pgs).
Examination Report dated Feb. 22, 2005 received in corresponding European Application No. 01932833.5 (3pages).
EPO Office Action dated Sep. 22, 2005 issued in corresponding European application 01932833.5-2310.
EPO Office Action dated Sep. 11, 2006 issued in corresponding European application 01932833.5-2310.
International Preliminary Examination Report dated Nov. 5, 2002 issued in corresponding PCT patent application No. PCT/US01/14061.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.
Japanese Notice of Reasons for Rejection dated Jun. 1, 2010 issued in related Japanese Patent Application No. 2003394702.
European Office Action dated Jun. 1, 2010 issued in related European Patent Application No. 04811836.8-2310.

Japanese Notice of Reasons for Rejection dated Jun. 29, 2010 issued in related Japanese Patent Application No. 2007519417.
Australian Office Action dated Jun. 11, 2010 issued in related Australian Patent Application No. 2005277078.
International Search Report dated Jun. 9, 2010 issued in related International Patent Application No. PCT/US2010/031594.
European Office Action dated May 7, 2010 issued in related European Patent Application No. 06733631.3-2310.
International Search Report dated Jun. 18, 2010 issued in related International Patent Application No. PCT/US2010/031602.
U.S. Office Action dated Jun. 8, 2010 issued in related U.S. Appl. No. 11/209,170.
U.S. Office Action dated Aug. 30, 2006 issued in related U.S. Appl. No. 10/618,887.
U.S. Office Action dated Jan. 15, 2008 issued in related U.S. Appl. No. 10/618,887.
U.S. Office Action dated May 18, 2009 issued in related U.S. Appl. No. 11/209,170.
U.S. Office Action dated May 28, 2009 issued in related U.S. Appl. No. 11/359,891.
U.S. Office Action dated May 13, 2009 issued in related U.S. Appl. No. 11/359,892.
International Search Report and Written Opinion dated Jun. 1, 2009 issued in related International Patent Application No. PCT/US2009/035889.
International Preliminary Report and Patentability dated May 7, 2009 issued in related International Patent Application No. PCT/US2007/082262.
Supplemental European Search Report dated May 28, 2009 issued in related International European Patent Application No. 01997077.1.
Supplemental European Search Report dated May 11, 2009 issued in related International European Patent Application No. 02805182.9.
Notice of Allowance dated Feb. 20, 2009 issued in related U.S. Appl. No. 10/618,887.
International Search Report and Written Opinion dated Apr. 21, 2010 issued in related International Patent Application No. PCT/US2010/025095.
International Search Report and Written Opinion dated May 3, 2010 issued in related International Patent Application No. PCT/US2010/025464.
European Office Action dated Apr. 13, 2010 issued in related European Patent Application No. 02805182.9-2310.
European Office Action dated Mar. 25, 2010 issued in related European Patent Application No. 01997077.1-2310.
U.S. Office Action dated May 18, 2010 issued in related U.S. Appl. No. 12/415,503.
McCarty, III., et al., "Nonarthoplasty Treatment of Glenohumeral Cartilage Lesions," Arthroscopy, The Journal of Arthroscopic and related Surgery, vol. 21, No. 9; Sep. 2005 (pp. 1131-1142).
Bushnell, et al., "Bony Instability of the Shoulder," Arthroscopy, The Journal of Arthroscopic and related Surgery, vol. 24, No. 9; Sep. 2005 (pp. 1061-1073).
Scalise, et al., "Resurfacing Arthroplasty of the Humerus: Indications, Surgical Technique, and Clinical Results," Techniques in Shoulder and Elbow Surgery 8(3):152-160; 2007.
Davidson, et al., "Focal Anatomic Patellofemoral Inlay Resurfacing: Theoretic Basis, Surgical Technique, and Case Reports," Orthop. Clin. N. Am., 39 (2008) pp. 337-346.
Provencher, et al., "Patellofemoral Kinematics After Limited Resurfacing of the Trochlea," The Journal of Knee Surgery, vol. 22 No. 2 (2008) pp. 1-7.
Dawson, et al., "The Management of Localized Articular Cartilage Lesions of the Humeral Head in the Athlete," Operative Techniques in Sports Medicine, vol. 16, Issue 1, pp. 14-20 (2008).
Uribe, et al., "Partial Humeral Head Resurfacing for Osteonecrosis," Journal of Shoulder and Elbow Surgery, (2009) 6 pages.
Burks, "Implant Arthroplasty of the First Metatarsalphalangeal Joint," Clin. Podiatr. Med. Surg., 23 (2006) pp. 725-731.
Hasselman, et al., "Resurfacing of the First Metatarsal Head in the Treatment of Hallux Rigidus," Techniques in Foot & Ankle Surgery 7(1):31-40, 2008.

Gelenkoberflachen, et al., "Partial hemi-resurfacing of the hip joint—a new approach to treat local osteochondral defects?" Biomed Tech 2006; 51:371-376 (2006).
Sullivan, "Hallux Rigidus: MTP Implant Arthroplasty," Foot Ankle Clin. N. Am. 14 2009) pp. 33-42.
Cook, et al., "Meta-analysis of First Metatarsophalangeal Joint Implant Arthroplasty," Journal of Foot and Ankle Surgery, vol. 48, Issue 2, pp. 180-190 (2009).
Derner, "Complications and Salvage of Elective Central Metatarsal Osteotomies," Clin. Podiatr. Med. Surg. 26 (2009) 23-35.
Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.
Beecher, et al. "Effects of a contoured articular prosthetic device on tibiofemoral peak contact pressure: a biomechanical study," Knee Surg Sports Traumatol Arthrosc. Jan. 2008; 16(1): 56-63.
United States Office Action dated May 13, 2009 issued in related U.S. Appl. No. 11/359,892.
United States Office Action dated May 18, 2009 issued in related U.S. Appl. No. 11/209,170.
United States Office Action dated May 1, 2009 issued in related U.S. Appl. No. 11/461,240.
Australian Office Action dated Jan. 29, 2009 issued in related Australian Patent Application No. 2004216106.
European Search Report dated Apr. 22, 2009 issued in related European Patent Application No. 09002088.4.
United States Office Action issued is related U.S. Appl. No. 10/760,965 dated Feb. 19, 2008.
Australian Office Action issued in related Australian Patent Application No. 2003262428 dated Mar. 20, 2008.
Australian Office Action issued in related Australian Patent Application No. 2004293042 dated Feb. 20, 2008.
U.S. Office Action dated Jan. 9, 2009 issued in related U.S. Appl. No. 10/373,463.
Canadian Office Action dated Dec. 9, 2008 issued in related Canadian Patent Application No. 2407440.
Supplemental European Search Report dated Nov. 6, 2008 issued in related European Patent Application No. 05791453.3-2310.
Japanese Office Action dated Dec. 19, 2008 issued in Japanese Patent Application No. 2006501193.
Japanese Office Action dated Jan. 13, 2009 issued in Japanese Patent Application No. 2003552147.
International Search Report dated Jan. 30, 2006 issued in related International Patent Application No. PCT/US04/39181.
U.S. Office Action dated Mar. 27, 2009 issued in related U.S. Appl. No. 11/169,326.
European Office Action dated Feb. 26, 2009 in related European Patent Application No. 05791453.3.
Australian Office Action dated Apr. 9, 2010 issued in related Australian Patent Application No. 2005260590.
U.S. Office Action dated Mar. 2, 2010 issued in related U.S. Appl. No. 11/169,326.
U.S. Office Action dated Mar. 9, 2010 issued in related U.S. Appl. No. 11/359,892.
Australian Office Action dated Feb. 26, 2010 issued in related Australian Patent Application No. 2008207536.
Supplemental Notice of Allowance dated Feb. 2, 2010 issued in related U.S. Appl. No. 10/373,463.
European office communication dated Feb. 10, 2010 issued in European Patent Application No. 09002088.4-2310.
U.S. Office Action dated Oct. 21, 2008 issued in related U.S. Appl. No. 11/461,240.
U.S. Office Action dated Jun. 25, 2008 issued in related U.S. Appl. No. 11/359,891.
U.S. Office Action dated Sep. 25, 2008 issued in related U.S. Appl. No. 11/326,133.
U.S. Office Action dated Jul. 2, 2008 issued in related U.S. Appl. No. 11/379,151.
European Office Action dated Oct. 6, 2008 issued in related European Patent Application No. 01932833.5-2310.

U.S. Office Action dated Jun. 27, 2008 issued in related U.S. Appl. No. 10/760,965.
International Search Report and Written Opinion dated Oct. 1, 2008 issued in related International Patent Application No. PCT/US08/53194.
International Search Report and Written Opinion dated Oct. 9, 2008 issued in related International Patent Application No. PCT/US07/82262.
European Search Report dated Nov. 4, 2008 issued in related European Patent Application No. 04811836.8-2310.
Habermeyer, "Eclipse, Schaftfreie Schulterprothese Operationsanleitung,".
US Office Action issued in related U.S. Appl. No. 10/994,453 dated Feb. 25, 2008.
U.S. Office Action dated Oct. 15, 2010 received in related U.S. Appl. No. 12/027,121.
U.S. Supplemental Notice of Allowance dated Oct. 28, 2010 issued in related U.S. Appl. No. 12/415,503.
European Search Report dated Nov. 4, 2010 issued in related European Patent Application No. 07862736.1-1269.
Cannulated Hemi Implants from Vielex, (3 pages).
Arthrosurface, Restoring the Geometry of Motion, HemiCAP Patello—Femoral Resurfacing System (19 pages).
Chuck (engineering),Wikipedia, the free encyclopedia, http://en.wikipedia.org/w/index.php?title=Chuck_%28engineering%29&printable=yes, Jun. 25, 2007, (4 pages).
Major Biojoint System, La nuova frontiera della biointegrazione naturale, Finceramica Biomedical solutions (4 pages).
Reversed Arthroplastie, Total Evolutive Shoulder System T.E.S.S., Biomet France, Biomet Europe (4 pages).
Notice of Allowance dated Sep. 9, 2010 issued in related U.S. Appl. No. 10/994,453.
Office Action dated Sep. 21, 2010 issued in related U.S. Appl. No. 11/169,326.
Office Action dated Sep. 29, 2010 issued in related U.S. Appl. No. 11/461,240.
Office Action dated Oct. 11, 2010 issued in related Australian Patent Application No. 2006216725.
International Preliminary Report on Patentability dated Sep. 16, 2010 issued in related International Patent Application No. PCT/US2009/035889.
Supplemental Notice of Allowance dated Oct. 13, 2010 issued in related U.S. Appl. No. 10/994,453.
Supplemental Notice of Allowance dated Oct. 6, 2010 issued in related U.S. Appl. No. 12/415,503.
U.S. Office Action issued in related U.S. Appl. No. 11/326,133 dated Jun. 12, 2008.
International Search Report and Written Opinion dated Jun. 24, 2008 issued in related International Patent Application No. PCT/US07/73685.
International Search Report and Written Opinion dated Jun. 11, 2008 issued in related International Patent Application No. PCT/US07/25284.
International Search Report and Written Opinion dated Aug. 8, 2008 issued in related International Patent Application No. PCT/US08/53988.
U.S. Office Action issued in related U.S. Appl. No. 10/994,453 dated Jun. 5, 2007.
Japanese Office Action dated Jul. 22, 2008 issued in related Japanese Patent Application No. 2006-501193.
U.S. Office Action issued in related U.S. Appl. No. 10/373,463 dated Apr. 21, 2008.
Notice of Allowance received in U.S. Appl. No. 10/618,887 dated Aug. 15, 2008.
Australia Office Action issued in related Australian Patent Application No. 2007216648 dated May 30, 2008.
European Office Action issued in related European Patent Application No. 01932833.5-2310 dated Apr. 25, 2008.
U.S. Office Action received in related U.S. Appl. No. 11/169,326 dated Jun. 30, 2008.
U.S. Office Action received in related U.S. Appl. No. 11/169,326 dated Jul. 27, 2007.
U.S. Office Action received in related U.S. Appl. No. 11/169,326 dated Apr. 17, 2007.
U.S. Office Action received in related U.S. Appl. No. 11/169,326 dated Mar. 9, 2007.
Canadian Office Action issued in related Canadian Patent Application No. 2546582 dated Aug. 21, 2008.
U.S. Office Action issued in related U.S. Appl. No. 10/994,453 dated Sep. 3, 2008.
Canadian Office Action dated Jul. 29, 2010 issued in related Canadian Patent Application No. 2470936.
Supplemental European Search Report dated Aug. 9, 2010 issued in related European Patent Application No. 04714211.2-2300.
Australian Office Action dated Aug. 23, 2010 issued in related Australian Patent Application No. 2006203909.
Office Action dated Sep. 2, 2010 issued in related U.S. Appl. No. 12/415,503.
Office Action dated Aug. 30, 2010 issued in related U.S. Appl. No. 12/397,095.
Office Action dated Jul. 21, 2010 issued in related U.S. Appl. No. 11/551,912.
Office Action dated Aug. 5, 2010 issued in related U.S. Appl. No. 11/325,133.
Notice of Allowance dated Aug. 6, 2010 issued in related U.S. Appl. No. 11/359,892.
Notice of Reasons for Rejection issued in related Japanese Patent Application No. 2003-394702 mailed Jul. 21, 2009.
Notice of Reasons for Rejection issued in related Japanese Patent Application No. 20-541615 mailed May 26, 2009.
International Preliminary Report on Patentability issued in related International Patent Application No. PCT/US2007/025284 dated Jun. 25, 2009.
Office Action issued in related Australian Patent Application No. 2007216648 dated Jul. 28, 2009.
European Search Report dated Jul. 10, 2009 issued in related European Patent Application No. 09002088.4.
Notice of Allowance issued in corresponding U.S. Appl. No. 10/618,887 dated Sep. 13, 2007.
International Preliminary Report on Patentability and Written Opinion dated May 22, 2006 in corresponding PCT patent application No. PCT/US04/039181.
English language translation of Japanese Office Action dated Aug. 9, 2007 issued in corresponding Japanese application No. 2003-552148.
Canadian Office Action dated Jan. 2, 2008 issued in corresponding Canadian Application No. 2407440.
International Preliminary Report on Patentability and Written Opinion dated Mar. 1, 2007 in corresponding PCT patent application No. PCT/US05/030120.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report dated Dec. 27, 2001 issued in corresponding PCT patent application No. PCT/US01/14061.
International Search Report dated May 23, 2003 issued in corresponding PCT patent application No. PCT/US02/40310.
International Search Report and Written Opinion dated Dec. 30, 2004 issued in corresponding PCT patent application No. PCT/US04/05539.
International Search Report and Written Opinion dated Jan. 30, 2006 issued in corresponding PCT patent application No. PCT/US04/39181.
International Search Report and Written Opinion dated Aug. 30, 2006 issued in corresponding PCT patent application No. PCT/US06/06323.
International Search Report and Written Opinion dated Sep. 29, 2006 issued in corresponding PCT patent application No. PCT/US05/30120.
International Search Report and Written Opinion dated Nov. 27, 2006 issued in corresponding PCT patent application No. PCT/US06/00380.

International Search Report and Written Opinion dated Nov. 29, 2006 issued in corresponding PCT patent application No. PCT/US05/023200.

International Search Report and Written Opinion dated May 22, 2007 issued in corresponding PCT patent application No. PCT/US05/05980.

International Search Report and Written Opinion dated Aug. 8, 2007 issued in corresponding PCT patent application No. PCT/US06/29875.

Notice of Allowance issued in corresponding U.S. Appl. No. 10/308,718 dated Sep. 11, 2006.

Office Action issued in corresponding U.S. Appl. No. 11/326,133 dated Oct. 17, 2007.

Office Action issued in corresponding U.S. Appl. No. 10/741,044 dated Oct. 26, 2005.

European Office Action dated Jan. 11, 2010 issued in related European Patent Application No. 2005218302.

U.S. Office Action dated Jan. 25, 2010 issued in related U.S. Appl. No. 11/326,133.

Notice of Reasons for Rejection dated Nov. 17, 2009 issued in Japanese Patent Application No. 2007-519417.

European Search Report dated Dec. 3, 2009 issued in related European Patent Application No. 06735827.5.

Extended Search Report dated Feb. 22, 2011 issued in European Patent Application No. 10012693.7, 8 pages.

Notice of Allowance dated Mar. 2, 2011 issued in Australian Patent Application No. 2008207536, 3 pages.

Notice of Allowance dated Mar. 15, 2011 issued in U.S. Appl. No. 11/551,912, 7pages.

U.S. Office Action dated Apr. 11, 2011 issued in U.S. Appl. No. 11/779,044, 10 pages.

Notice of Allowance dated Apr. 28, 2011 issued in U.S. Appl. No. 12/027,121, 9 pages.

U.S. Office Action dated Sep. 2, 2009 issued in relation U.S. Appl. No. 10/994,453.

U.S. Office Action dated Oct. 5, 2009 issued in relation U.S. Appl. No. 10/789,545.

U.S. Office Action dated Oct. 15, 2009 issued in relation U.S. Appl. No. 11/551,912.

U.S. Office Action dated Oct. 14, 2009 issued in relation U.S. Appl. No. 11/461,240.

International Preliminary Report on Patentability dated Aug. 20, 2009 issued in related International Patent Application No. PCT/US2008/053194.

Australian Notice of Allowance dated Oct. 29, 2009 issued in related Australian Patent Application No. 2007216648.

Notice of Allowance dated Oct. 9, 2009 issued in related U.S. Appl. No. 10/373,463.

Australian Office Action dated Oct. 29, 2009 issued in related Australian Patent Application No. 2007203623.

Japanese Notice of Reasons for Rejection dated Sep. 8, 2009 issued in related Japanese Patent Application No. 2003552147.

Bale, MD, Reto J., et al, "Osteochondral Lesions of the Talus: Computer=assisted Retrograde Drilling Feasibility and Accuracy in Initial Experriences[1]", (Radiology. 2001;218:278-282) © RSNA, 2001.

Biomet/Copeland, "Aequalis® Resurfacing Head" Tornier, Scientific Vision, Surgical Leadership, SS-401 Jan. 2007.

Kumai, M.D., Tsukasa, et al Arthroscopic Drilling for the Treatment of Osteochondral Lesions of the Talus, The Journal of Bone & Joint Surgery, American vol. 81:1229-35(1999).

Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 Jul.-Aug. 2001:pp. 653-659.

Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.

Schneider, T., et al, "Arthroscopy of the ankle joint. A list of indications and realistic expectations", Foot and Ankle Surgery 1996 2:189-193, © 1996 Arnette Blackwell SA.

Taranow WS, et al, "Retrograde drilling of osteochondral lesions of the medial talar dome", PubMed, www.pubmed.gov, A service of the National Library of Medicing and the Natinal Institutes of Health, Foot Ankle Int.Aug. 1999; 20 (8):474-80.

Ueblacker, M.D., Peter, et al, "Retrograde Cartilage Transplantation of the Proximal and Distal Tibia", Arthroscopy: The Journal of Arthroscipic and Related Surgery, vol. 20, No. 1 Jan. 2004: pp. 73-78.

PCT International Preliminary Report on Patentability dated Sep. 9, 2011 issued in PCT Patent Application No. PCT/US2010/025464, 7 pages.

International Search Report and Written Opinion dated May 19, 2011 issued in PCT Application No. PCT/US2011/027451, 11 pages.

Canadian Notice of Allowance dated Jun. 1, 2011 issued in Canadian Patent Application No. 2,470,936, 1 page.

Examiner interview summary dated Jul. 1, 2011 issued in European Patent Application No. 02 805 182.9, 3 pages.

U.S. Office Action dated May 11, 2011 issued in U.S. Appl. No. 12/001,473, 18 pages.

U.S. Office Action dated May 16, 2011 issued in U.S. Appl. No. 12,582,345, 9 pages.

U.S. Final Office Action dated Jul. 8, 2011 issued in U.S. Appl. No. 11/169,326, 26 pages.

Ascension Orthopedics, Inc., Ascension Orthopedics Announces Market Release of TITIAN™ Inset Mini Glenoid, PR Newswire, downloaded from internet Jul. 18, 2011, http://www.orthospinenews.com/ascension-orthopedics-announces-market-release-of-titan™-inset-mini-glenoid, Jul. 6, 2011, 2 pages.

International Preliminary Report on Patentability dated Sep. 1, 2011 issued in PCT International Patent Application No. PCT/US2010/025095, 8 pages.

International Preliminary Report on Patentability dated Oct. 27, 2011 issued in PCT International Patent Application No. PCT/US2010/031602, 8 pages.

International Preliminary Report on Patentability dated Oct. 27, 2011 issued in PCT International Patent Application No. PCT/US2010/031594, 7 pages.

U.S. Office Action dated Nov. 1, 2011 issued in U.S. Appl. No. 12/713,135, 10 pages.

U.S. Office Action dated Nov. 28, 2011 issued in U.S. Appl. No. 12/711,039, 6 pages.

Habermeyer, Peter, ATOS News, Oct. 2005, "The Artificial Limb "Eclipse"—A new draft without shank in the implantation of artificial shoulder limbs", cover page w/pp. 40-41, with English translation dated Jan. 13, 2006 (2 pgs).

Thermann, et al, ATOS Newsletter, Jun. 2005, Aktuelle Themen, (16 pages).

Gray, Henry, Anatomy of the Human Body, 1918, 6d. The Foot 1. The Tarsus, II. Osteology, cover page and 12 pgs, ww. Bartleby.com/107/63.html#i268 Oct. 25, 2004.

Chainsaw, Wikipedia, the free encyclopedia, http://en.wikipedia.org/w/index.php?title=Chainsaw&printable=yes, Jun. 26, 2007 (3 pages).

Cannulated Hemi Implants from Vielex, (3 pages), Oct. 30, 2007
APTA | Knee,/http://www.apta.org/AM/PrinerTemplate.cfm?Section=Home&TEMPLATE=/CM/HTMLDisplay.dfg&... Jun. 25, 2007 (1page).

Arthrosurface, Restoring the Geometry of Motion, HemiCAP Patello—Femoral Resurfacing System (19 pages) Oct. 30, 2007.

Anatomical Arthroplastie, Total Evolutive Shoulder System T.E.S.S., Biomet France, Biomet Europe (4 pages).

American Machinist, Full-radius milling cutters, http://www.americanmachinist.com/Classes/Article/ArticleDraw_P. aspx, Jun. 26, 2007 (1 page).

Chuck (engineering),Wikipedia, the free encyclopedia, http://en.wikipedia.org/w/index.php?title=Chuck_%28engineering%29&printable=yes, Jun. 25, 2007, (4 pages).

Dovetail Rails, http://www.siskiyou.com/MDRSeries.htm, Jun. 25, 2007 (2 pages).

Knee Resurfacing, Permedica, GKS, Global Knee System. Cod. 104570 vers 1.0 del Mar. 15, 2006 (8pages).

Major Biojoint System, La nuova frontiera della biointegrazione naturale, Finceramica Biomedical solutions (4 pages), Oct. 30, 2007.

Makita Industrial Power Tools, Product Details Print Out, Chain Mortiser, http://www.makita.com/menu.php?pg=product_det_prn&tag=7104L, Jun. 26, 2007 (3pgs).

Milling machine, Wikipedia, the free encyclopedia, http://en.wikipedia.org/w/index.php?title=Milling_machine&printable=yes, Jun. 26, 2007 (4 pages).

Mortise and tenon, Wikipedia, the free encyclopedia, http://en.wikipedia.org/w/index.php?title=Mortise_and_tenon&printable=yes, Jun. 25, 2007 (3 pages).

Oka et al, "Development of artificial articular cartilage", Proc Instn Mech Engrs vol. 214 Part H, 2000 pp. 59-68 (10 pages).

Reversed Arthroplastie, Total Evolutive Shoulder System T.E.S.S., Biomet France, Biomet Europe (4 pages), Oct. 30, 2007.

M. Siguier, MD et al, "Preliminary Results of Partial Surface Replacement of the Femoral Head in Osteonecrosis", The Jorunal of Arthroplasty, vol. 14, No. 1, 1999, pp. 45-51.

T. Siguier, MD et al, Partial Resurfacing Arthroplasty of the Femoral Head in Avascular Necrosis, Clinical Orthopaedics and Related Research, No. 386, 2001, pp. 85-92.

Suganuma, et al—"Arthroscopically Assisted Treatment of Tibial Plateau Fractures", Arthroscopy: The Journal of Arthroscopic and Related Surgery, vol. 20, No. 10, Dec. 2004, pp. 1084-1089 (6 pages).

The Mini Uni: A New Solution for Arthritic Knew Pain and Disability, AORI, 4 pages, www.aori.org/uniknee.htm Apr. 20, 2004.

The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.

Ushio et al, "Partial hemiarthroplasty for the treatment of osteonecrosis of the femoral hear", An Experimantal Study in the Dog, The Journal of Bone and Joint Surgery, vol. 85-B, No. 6, Aug. 2003, pp. 922-930 (9 pages).

Russell E. Windsor, MD, In-Depth Topic Reviews, Unicompartmental Knee Replacement, Nov. 7, 2002, 9 pages.

Yaw angle, Wikipedia, the free encyclopedia, http://en.wikipedia.org/w/index.php?title=Yaw_angle&printable=yes, Jun. 25, 2007 (1 page).

European Office Action dated Jan. 23, 2012 issued in European Patent Application No. 01 997 077.1, 3 pages.

Notice of Allowance dated Feb. 24, 2012 issued in U.S. Appl. No. 12/027,121, 9 pages.

Supplemental Notice of Allowance dated Mar. 2, 2012 issued in U.S. Appl. No. 12/027,121, 2 pages.

Office Action dated Mar. 2, 2012 issued in U.S. Appl. No. 12/713,135, 7 pages.

Examination Report dated Dec. 30, 2011 issued in European Patent Application No. 09 002 088.4, 6 pages.

Intent to Grant dated Feb. 17, 2012 issued in European Patent Application No. 02 805 182.9, 5 pages.

Intent to Grant dated Feb. 29, 2012 issued in European Patent Application No. 10 012 693.7, 5 pages.

Notice of Allowance dated Dec. 12, 2011 issued in U.S. Appl. No. 12/582,345, 19 pages.

U.S. Office Action dated Dec. 27, 2011 issued in U.S. Appl. No. 12/620,309, 10 pages.

U.S. Office Action dated Jan. 4, 2012 issued in U.S. Appl. No. 12/001,473, 19 pages.

U.S. Office Action dated Jan. 10, 2012 issued in U.S. Appl. No. 12/031,534, 9 pages.

U.S. Office Action dated Jan. 18, 2012 issued in U.S. Appl. No. 12/778,055, 9 pages.

International Preliminary Report on Patentability dated Aug. 20, 2009 issued in related International Patent Application No. 2008053194.

Notice of Allowance dated Aug. 25, 2009 issued in related U.S. Appl. No. 11/379,151.

Notice of Allowance dated Aug. 27, 2009 issued in related U.S. Appl. No. 10/760,965.

U.S. Office Action dated Mar. 29, 2012 issued in U.S. Appl. No. 10/789,545, 7 pages.

U.S. Office Action dated Apr. 18, 2012 issued in U.S. Appl. No. 12/725,181, 9 pages.

U.S. Office Action dated Aug. 28, 2012 issued in U.S. Appl. No. 12/762,948, 12 pages.

U.S. Notice of Allowance dated Sep. 4, 2012 issued in U.S. Appl. No. 11/169,326, 6 pages.

Preliminary Report on Patentability dated Sep. 20, 2012 issued in PCT Patent Application No. PCT/US2011/027451, 3 pages.

Extended European Search Report dated Dec. 10, 2012 issued in European Patent Application No. 08449.1, 6 pages.

U.S. Office Action dated Feb. 25, 2013 issued in U.S. Appl. No. 12/762,920, 8 pages.

Final Office Action dated Aug. 13, 2012 issued in U.S. Appl. No. 12/711,039, 12 pages.

Office Action dated Aug. 14, 2012 issued in U.S. Appl. No. 12/001,473, 17 pages.

Office Action dated Aug. 20, 2012 issued in U.S. Appl. No. 13/037,998, 11 pages.

Office Action dated Aug. 21, 2012 issued in U.S. Appl. No. 13/043,430, 11 pages.

Extended Search Report dated Jul. 3, 2012 issued in European Patent Application No. 12002103.5, 5 pages.

Decision to Grant dated Jul. 26, 2012 issued in European Patent Application No. 10012693.7, 1 page.

Notice of Allowability dated Oct. 9, 2012, issued in U.S. Appl. No. 12/713,135, 5 pages.

Notice of Allowability dated Oct. 11, 2012, issued in U.S. Appl. No. 11/169,326, 2 pages.

U.S. Office Action dated Oct. 23, 2012, issued in U.S. Appl. No. 13/042,382, 17 pages.

U.S. Office Action dated Oct. 24, 2012, issued in U.S. Appl. No. 12/942,923, 9 pages.

U.S. Office Action dated Oct. 31 2012, issued in U.S. Appl. No. 13/075,006, 9 pages.

Notice of Allowance dated Nov. 13, 2012 issued in U.S. Appl. No. 12/725,181, 5 pages.

Extended European Search report mailed Dec. 10, 2012 issued in European Patent Application No. 07844549.1, 6 pages.

Supplementary European Search Report dated Jan. 3, 2013 issued in European Patent Application No. 05763817.3, 3 pages.

Great Britain Examination Report dated Feb. 6, 2013 issued in Great Britain Patent Application No. 1114417.7, 2 pages.

Supplementary European Search Report dated Feb. 18, 2013 issued in European Patent Application No. 08729178.7, 10 pages.

Canadian Office Action dated Dec. 13, 2012 issued in Canadian Patent Application No. 2,407,440, 6 pages.

International Search Repoort and Written Opinion dated Mar. 8, 2013 issued in PCT Patent Application No. PCT/US12/71199, 13 pages.

U.S. Office Action dated Apr. 15, 2013 issued in U.S. Appl. No. 13/470,678, 10 page.

U.S. Office Action dated Apr. 22, 2013 issued in U.S. Appl. No. 12/001,473, 16 page.

U.S. Office Action dated Apr. 23, 2013 issued in U.S. Appl. No. 13/037,998, 8 page.

European Intent to Grant dated Apr. 29, 2013 issued in European Patent Application No. 07 862 736.1, 7 pages.

U.S. Notice of Allowance dated May 9, 2013 issued in U.S. Appl. No. 12/725,181, 6 pages.

U.S. Office Action dated May 15, 2013 issued in U.S. Appl. No. 12/762,948, 10 pages.

European Office Action dated Apr. 16, 2013 issued in European Patent Application No. 12 002 103.5, 5 pages.

European Office Action date May 15, 2013 issued in European Patent Application No. 05 763 817.3, 4 pages.

U.S. Applicant Initiated Interview Summary dated May 15, 2013 issued in U.S. Appl. No. 12/762,920, 3 pages.

U.S. Final Office Action dated Jun. 5, 2013 issued in U.S. Appl. No. 12/942,923, 26 pages.

U.S. Final Office Action dated Jun. 24, 2013 issued in U.S. Appl. No. 13/042,382, 28 pages.

U.S. Notice of Allowance dated Jun. 14, 2013 issued in U.S. Appl. No. 13/043,430, 10 pages.

* cited by examiner

TIBIAL RESURFACING SYSTEM

CROSS-REFERENCE TO RELATED APPLICATIONS

This application is a divisional of U.S. patent application Ser. No. 10/308,718, filed Dec. 3, 2002, now U.S. Pat. No. 7,163,541, the teachings of which are incorporated herein by reference.

FIELD OF THE INVENTION

The present invention relates generally to the field of orthopedic joint replacement, and particularly, to the field of orthopedic joint replacement of the knee.

BACKGROUND OF THE INVENTION

In the field of orthopedic joint replacement of the knee, a relatively recent evolution of the art has resulted in prosthetics that require less removal of bone stock as the preparation for the implantation of the prosthetic devices. This trend in technique and prosthetic design is primarily aimed at creating more options for the orthopedic surgeon when challenged with treating a young active individual with joint disease. It has now become well accepted that treating this individual with a total joint arthroplasty (prosthetic) will be an effective way of relieving the symptoms of pain, but this younger patient will likely place demands on his prosthetic joint that will result in the rapid wear, loosening, and need for replacement of the implants.

In the natural knee, loads transmitted to the joint surfaces during normal activities such as running, walking, and jumping create harsh environments for the articular surface tissues. These articular surface tissues consisting of hyaline cartilage play a key role in the load distribution and impact absorption capability of the knee. The wear and degradation of these tissues is typically the endpoint, which creates symptoms of pain and eventually drives an individual to consider joint replacement surgery.

However, many structures and tissues in the joint as well as the musculature of the leg play a complex role in the distribution and management of the loads ultimately seen by the articular surfaces. Arguably one of the most important of these is the meniscus. The meniscus is a kidney-bean shaped structure which attaches to the top articular surface of the tibia with two bony inserts, one anteriorly and one posteriorly. The meniscus is contoured so that it matches the surface of the tibial articular surface on its underside and matches the convex curve of the mating femoral articular surface on its topside. It is comprised of a highly organized system of fibrous bands that are circumferential and give the structure its hoop strength characteristics. In this capacity, the meniscus is understood to significantly increase the contact surface area of the joint so that loads are more evenly distributed over a greater area of both the femoral and tibial hyaline cartilage surfaces. For this reason, there is great advantage to try to preserve this structure.

In prosthetic knee joints, one of the greatest causes of failure is based on wear debris of the tibial component. Not only does this result in the wear of the tibial component but also produces small wear debris particles which stimulate osteolysis, inflammatory changes in neighboring tissues, and eventual loosening of the implant.

Modern prosthetic joint design relies on a careful contour matching of the tibial component, typically composed of ultra-high molecular weight polyethylene (UHMWPE), to the femoral component, typically composed of a Cobalt-Chrome Alloy (CoCr). Mismatch of the surfaces or misalignment of the surfaces during surgical implantation will cause accelerated wear and early failure of the joint. However, as a function of the complex mechanics of the knee, even in the event of perfect surgical matching and alignment of the two components, there are still articulations of the prosthetic joint that create very concentrated local or even point loads between the two components, which result in the creation of a shear particle from the UHMWPE surface.

There would be a great advantage in developing a tibial component prosthetic component that could be implanted without requiring the removal of the meniscus. This component could effectively resurface only a portion of the overall tibial surface, so that the worn exposed portion of the tibial articular cartilage would be replaced, but areas of the tibial surface underlying the meniscus, and the insertion sites of the meniscus would remain intact. This implant would preserve as much normal knee anatomy and load bearing tissue as possible in an attempt to eliminate concentrated loads or point loads between a femoral component (as appears in previous patents) and the described tibial component. A system of instruments useful in locating, positioning and delivering the prosthetic is included.

SUMMARY OF THE INVENTION

Accordingly, in one aspect the present invention provides a drill guide for positioning a drill along an axis defined through a tibia bone and through a superior tibial surface, the axis is formed at an angle with respect to the long axis of the tibia, and the superior tibial surface bounded at least partially by a meniscus of a knee. The drill guide includes a targeting ring portion having at least one dimension sized to be equal to or less than the superior tibial surface bounded by the meniscus of the knee.

In another aspect, the present invention provides a bone chisel that includes an elongated tubular structure having a first end and a bone-cutting end. The bone-cutting end is terminated in a transverse angle thereby creating an elliptical bone-cutting face.

In other aspects, the present invention provides an articular surface implant that includes an angled bearing element comprising a cylindrical member having a first end and a second end. The first end is formed at an angle that creates an elliptical face of the first end, and the first end defines a load-bearing surface of an articular surface.

In yet another aspect, the present invention provides an articular surface implant that includes an angled bearing element, a fixation element adapted to engage bone, and an intermediate mount element adapted to couple the angled bearing element to the fixation element.

In other aspects, the present invention provides an articular surface implant that includes an angled bearing element comprising a cylindrical member having a first end and a second end. The first end is formed at an angle that creates an elliptical face of the first end, and the first end defines a load-bearing surface of an articular surface. The cylindrical member also includes means formed thereon to engage bone.

It will be appreciated by those skilled in the art that although the following Detailed Description will proceed with reference being made to exemplary embodiments and methods of use, the present invention is not intended to be limited to these exemplary embodiments and methods of use. Rather, the present invention is of broad scope and is intended to be limited as only set forth in the accompanying claims.

Other features and advantages of the present invention will become apparent as the following Detailed Description proceeds, and upon reference to the Drawings, wherein like numerals depict like parts, and wherein:

DETAILED DESCRIPTION OF EXEMPLARY EMBODIMENTS

Figure 1:
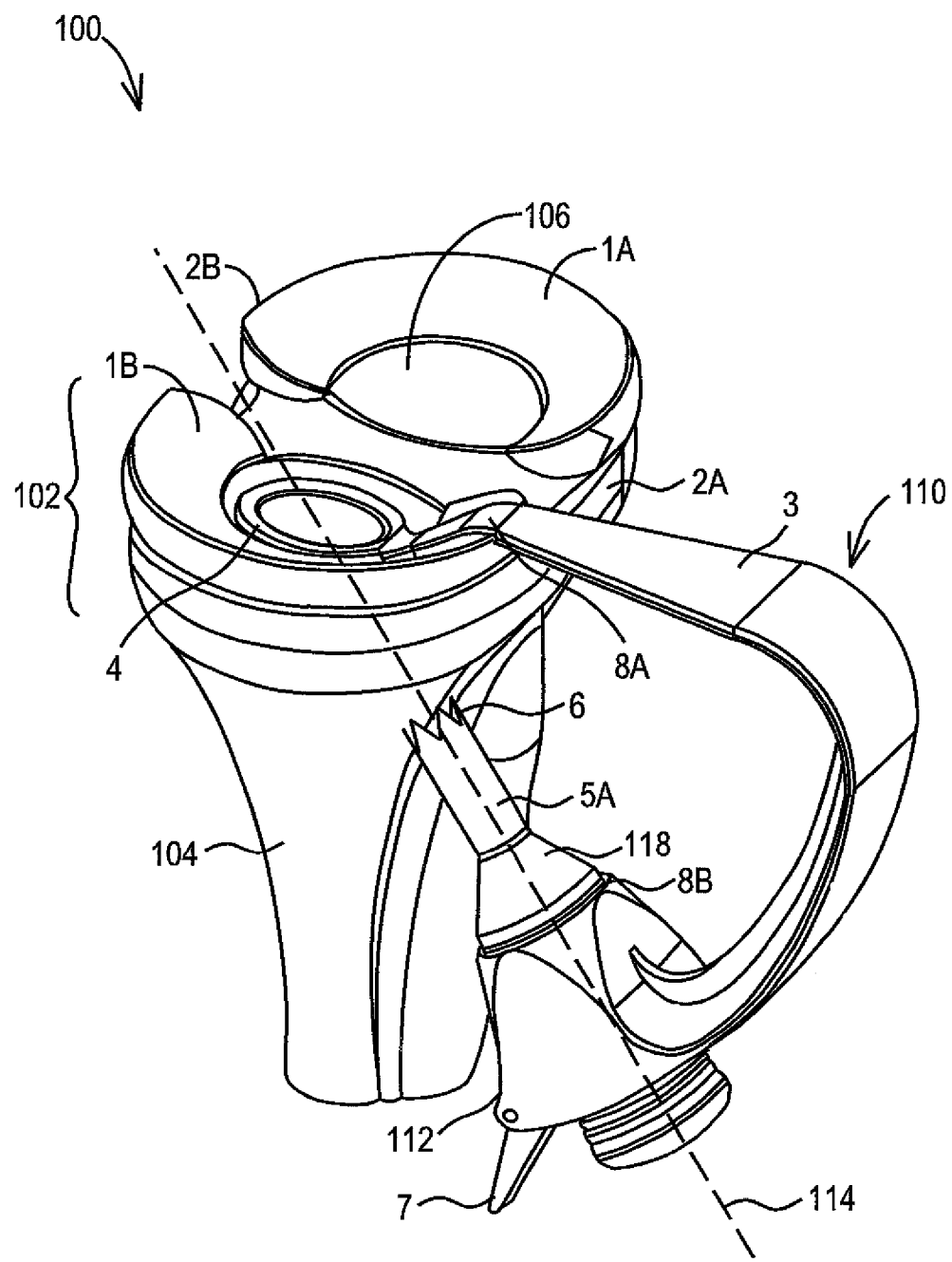
FIG. 1 is an in situ view of one exemplary drill guide according to the present invention.

FIG. 1 is an in situ view 100 of one exemplary drill guide according to the present invention. This figure depicts the proximal portion 102 of the tibia as well as the distal tibia 104. The knee contains a meniscus 1A and 1B in both the lateral and medial compartments, respectively. The meniscus is connected to the superior tibial surface by way of an anterior 2A and posterior 2B bony attachment. The meniscus is otherwise relatively mobile and glides along the top of the tibia 104 in concert with and as a partial constraint to the femoral condyle (not shown, but well understood in the art).

In one aspect of the present invention, a novel drill guide is provided. In one exemplary embodiment, a drill guide 10 is depicted in FIG. 1. The drill guide 10 of this exemplary embodiment generally includes a targeting ring 4, and angled boom 8A, a curved arm section 3 and a bore section 112. The targeting ring 4 may have a thickness that is narrow enough to be inserted between the femoral condyles and the superior tibial surface 106. The ring 4 may also be dimensioned to be approximately the same size and shape as the oval shaped implant that will eventually be delivered to the joint surface, as described more fully below. However, this is not a requirement of the present and only represents an exemplary shape of the ring.

The ring 4 is attached to the curved arm section 3 of the guide by an angled boom 8A that is configured to pass over the top of the meniscus 1B when the joint is accessed from one of two standard incisions used during arthroscopic surgery, the anterior-medial or anterior-lateral portal (these incisions are not depicted in FIG. 1, but are well understood in the art). The guide also contains a bore section 112 connected to the arm 3. In the exemplary embodiment, the bore section 112 is connected to the arm so that it creates an axis 114 that extends back through a center-point or near center-point within the central portion 116 of the oval targeting ring 4. The bore section 112 includes a hollow chuck 8B, a hollow collar taper 118 and a cylindrical bullet 5A. The bore section is sized to receive the cylindrical bullet. The cylindrical bullet 5A may be advanced within the chuck 8B until contact is made with bone surface of the tibia 104. To that end, the bullet 5A may include teeth 6 to enhance or secure contact with the bone surface of the tibia. A releasable ratchet 7 allows for advancement of the bullet 5A through the chuck 8B, and provides a locking mechanism to secure the bullet 5A into position to form a stable platform for subsequent steps.

Figure 3:
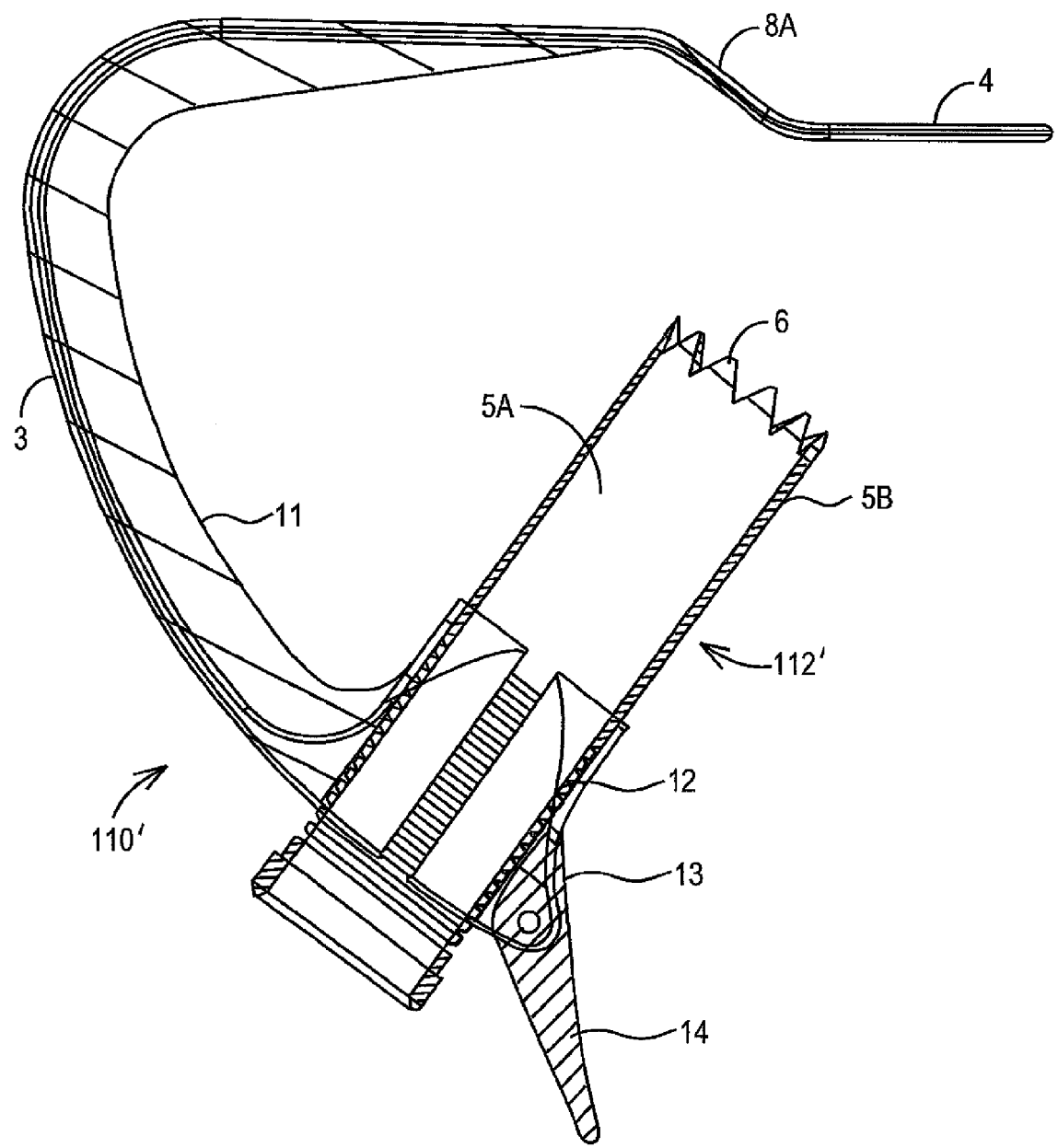
FIG. 3 is a side view of one exemplary drill guide according to the present invention.

FIG. 3 is a side view of another exemplary drill guide 110' according to the present invention. The arm section 3 may also include a stiffening central flange 11 in the arcuate portions of the arm 3. An alternative large bore bullet 5B may also be used in the guide. With either bullet (5A or 5B), the releasable ratchet mechanism may consist of a pawl 13 mounted pivotally on the chuck 8B. The bullet 5A or 5B may include a rack 12 generally defined as teeth on the side surface of the bullet. A portion of the pawl 14 may be loaded to pivotally actuate the pawl and disengage it from the rack.

Figure 2:
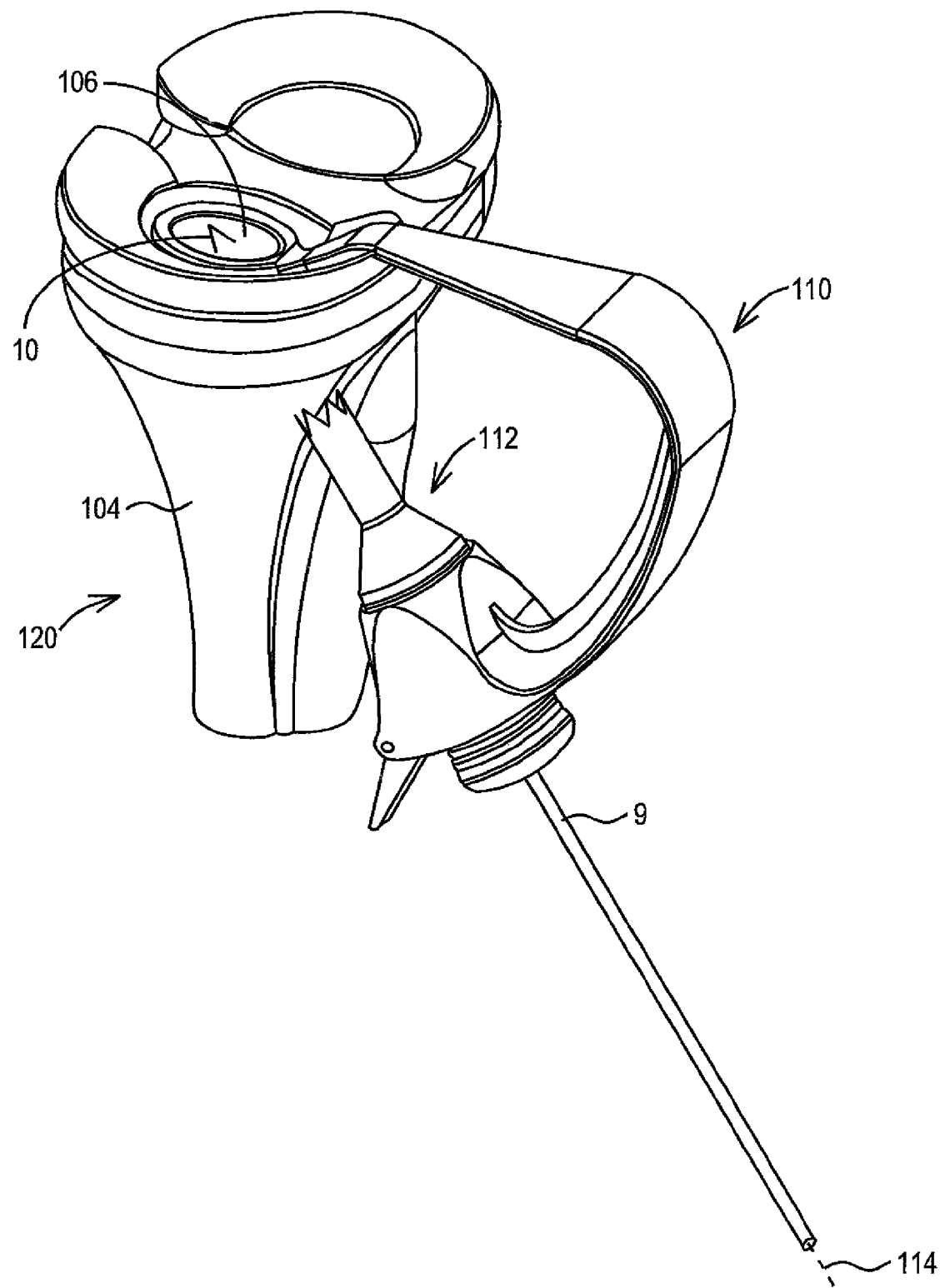
FIG. 2 is an in situ view of one exemplary drill guide and guide pin according to the present invention.

FIG. 2 is an in situ view 120 of one exemplary drill guide and guide pin according to the present invention. With the guide 110 in position, a guide pin 9 is inserted through the bore section 112 and drilled into the tibia 104. Preferably, the guide pin is drilled through the tibia along the axis 114 defined by the position of the bore section until the tip 10 of the drill 9 is visible in the center of the targeting ring 4.

Figure 4:
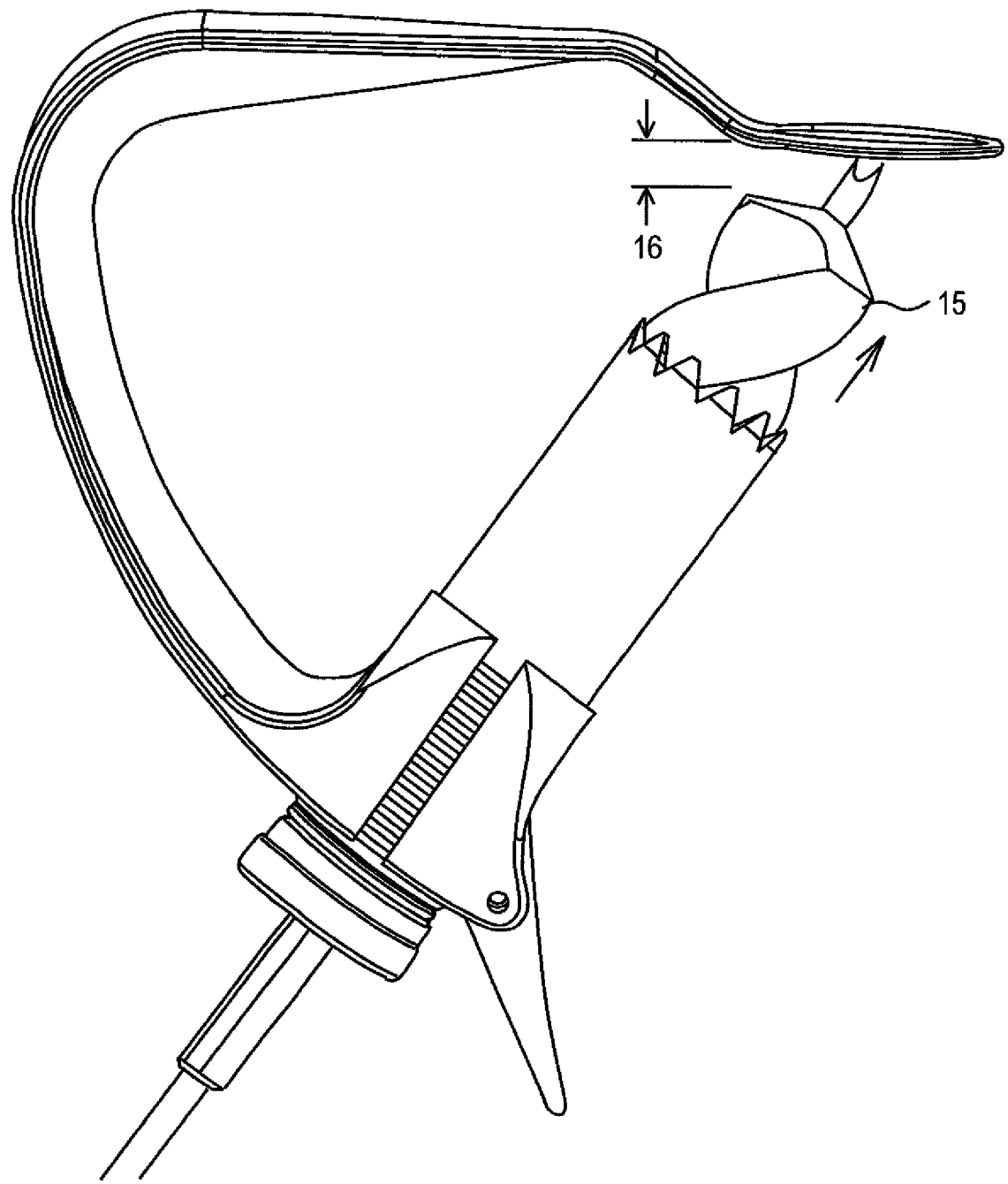
FIG. 4 is a side view of one exemplary drill guide and drill bit according to the present invention.

Referring now to FIG. 4, and once the guide pin 9 is properly positioned, a drill 15 is driven over the pin 9. In FIG. 4, the anatomical references are removed for clarity. The drill may have a diameter slightly larger than the diameter of implant (described below). In the exemplary embodiment, the drill is driven until it reaches a distance 16 that may be approximately 2-3 mm below the surface of the tibial articular surface 106. Techniques for determining this appropriate drilling distance based on a readable scale, or techniques including built in depth-stops in the guide or drill shaft are well described in the orthopedic art, and may be employed in the present invention. The drill utilized herein may be a conventional bone drill as is well understood in the art.

Figure 5:
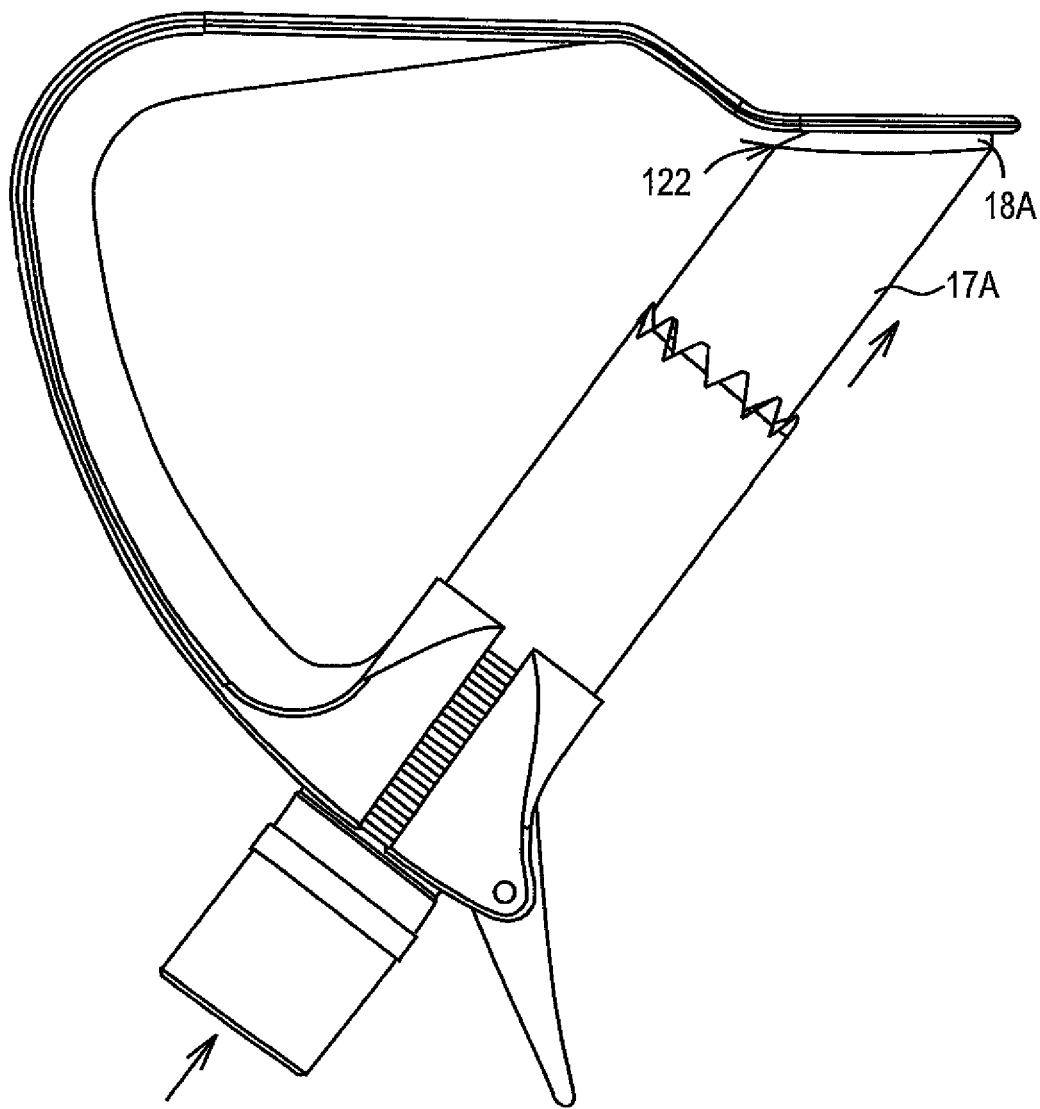
FIG. 5 is a side view of one exemplary drill guide and chisel according to the present invention.
Figure 6:
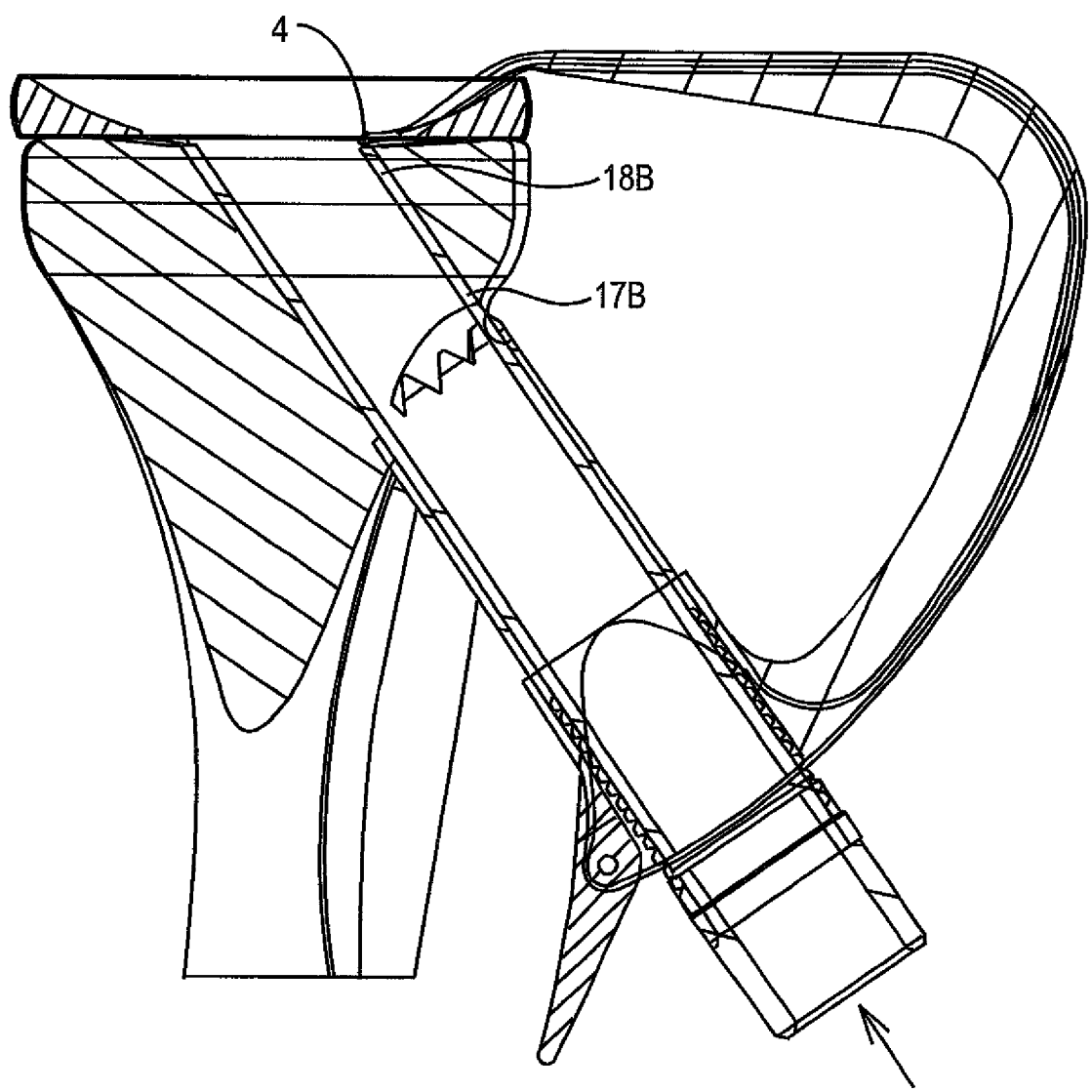
FIG. 6 is an in situ side view of one exemplary drill guide and chisel according to the present invention.

Next as depicted in FIG. 5, a cylindrical chisel 17A is introduced into the drilled tunnel and advanced up to the point were it contacts the end point of the previously drilled tunnel. This chisel of this exemplary embodiment includes a tip configuration comprising an angled transverse cut 122 across the chisel diameter. The chisel is essentially an elongated tubular structure, and the angled transverse cut 122 creates an elliptical end face 18A to the tube section. This elliptical geometry may correspond to the elliptical geometry of the tibial implant to be delivered, as well as the elliptical configuration of the targeting ring 4 of the drill guide. The chisel may include a beveled, sharp, tube tip, as depicted. Although not shown in the drawings, the chisel may include markings or keyed portions so that it will be driven in the proper rotational position relative to the oval targeting ring 19. To that end, the bore section 112 may include a key arrangement that is mated with the key on the chisel.

With the guide 110 held firmly in position, the chisel is impacted up to and against the underside surface of the targeting ring 4. To assist in the clean cutting of the bone and cartilage, the chisel and targeting ring may include some features (18B, to assist in the final alignment or cleaving of the compressed tissues.

Figure 7:
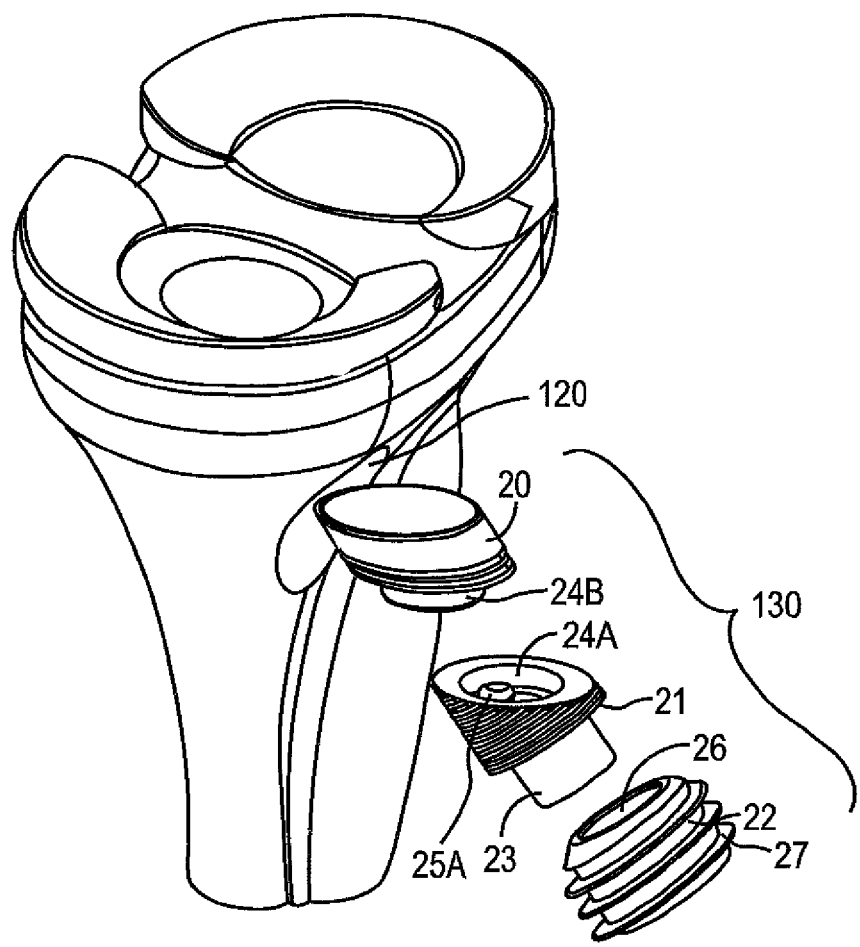
FIG. 7 is an exploded view of one exemplary implant according to the present invention.

The site is now prepared for implant delivery. FIG. 7 depicts an exploded view of one exemplary implant 130 according to the present invention. The implant 130 of the present invention is generally a cylindrical member that includes an angled bearing element comprising having a first end and a second end, where the first end is formed at an angle that creates an elliptical face of said first end. The first end defines a load-bearing surface of an articular surface. The implant may include three components, an angled bearing surface 20, an intermediate mount 21, and a fixation element 22. The bearing surface 20 may be fixed into the mount, for example, by a press-fit or snap-fit configuration between mating portions 24A, 24B of the underside of the bearing surface portion and the intermediate mount, respectively. An off-center boss 25A may be included in the mating portion 24A that fits into a matching off-center bore in the mating portion 24B of the bearing surface 20, to provide a rotational keying or alignment of the two components. Of course, the boss 25A may equally be provided in the mating portion 24B of the bearing surface 20. Those skilled in the art will recognize that numerous mechanical modifications may be made to the bearing surface 20 and/or intermediate mount 21 to provide rotational keying and/or alignment, and all such alternatives are deemed within the scope of the present invention. When the two components are assembled, a relatively continuous cylindrical shaft of the two components is formed.

Figure 8:
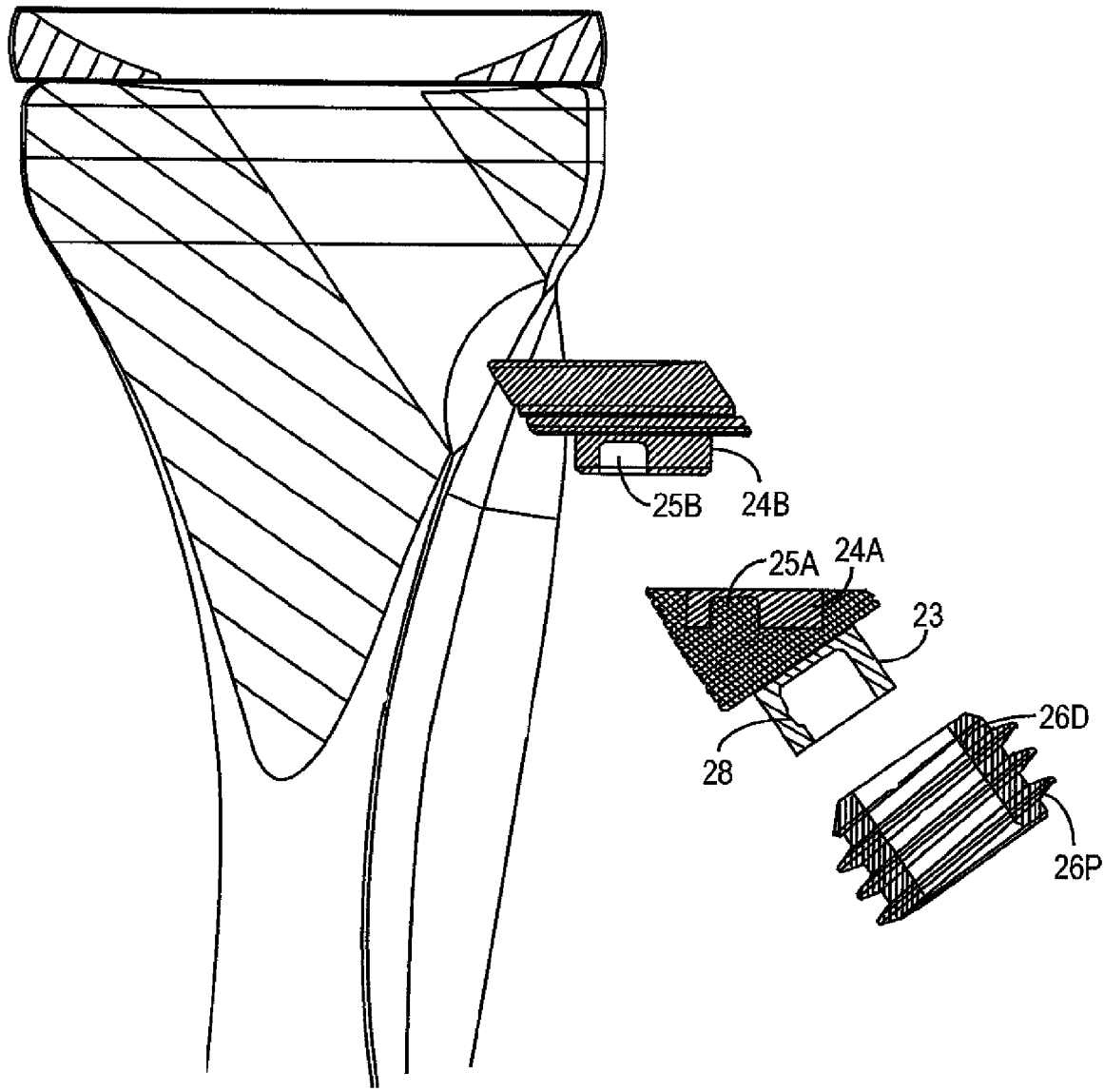
FIG. 8 is an exploded view of one exemplary implant according to the present invention.

FIG. 8 depicts an exploded cross-sectional view of the implant. The fixation element 22 of this exemplary embodiment is a screw with a modified cancellous thread form 27 and a root diameter that is approximately the same as the diameters of the bearing surface and the mount. In the exemplary embodiment, the root diameter is on the order of 10-20 mm. The screw has a large thru-hole 26 at the proximal end of the screw, and a taper bore 26D at the distal end of the screw which mates and interlocks to the male taper boss 23 on the proximal end of the mount component 21. When the two components 21,22 are forced together, the taper surfaces 26D and 23 will interlock forming a rigid connection between the two components. The proximal end of the screw also contains a hex bore 26P suited for engagement with a large orthopedic male hexdriver.

Figure 9:
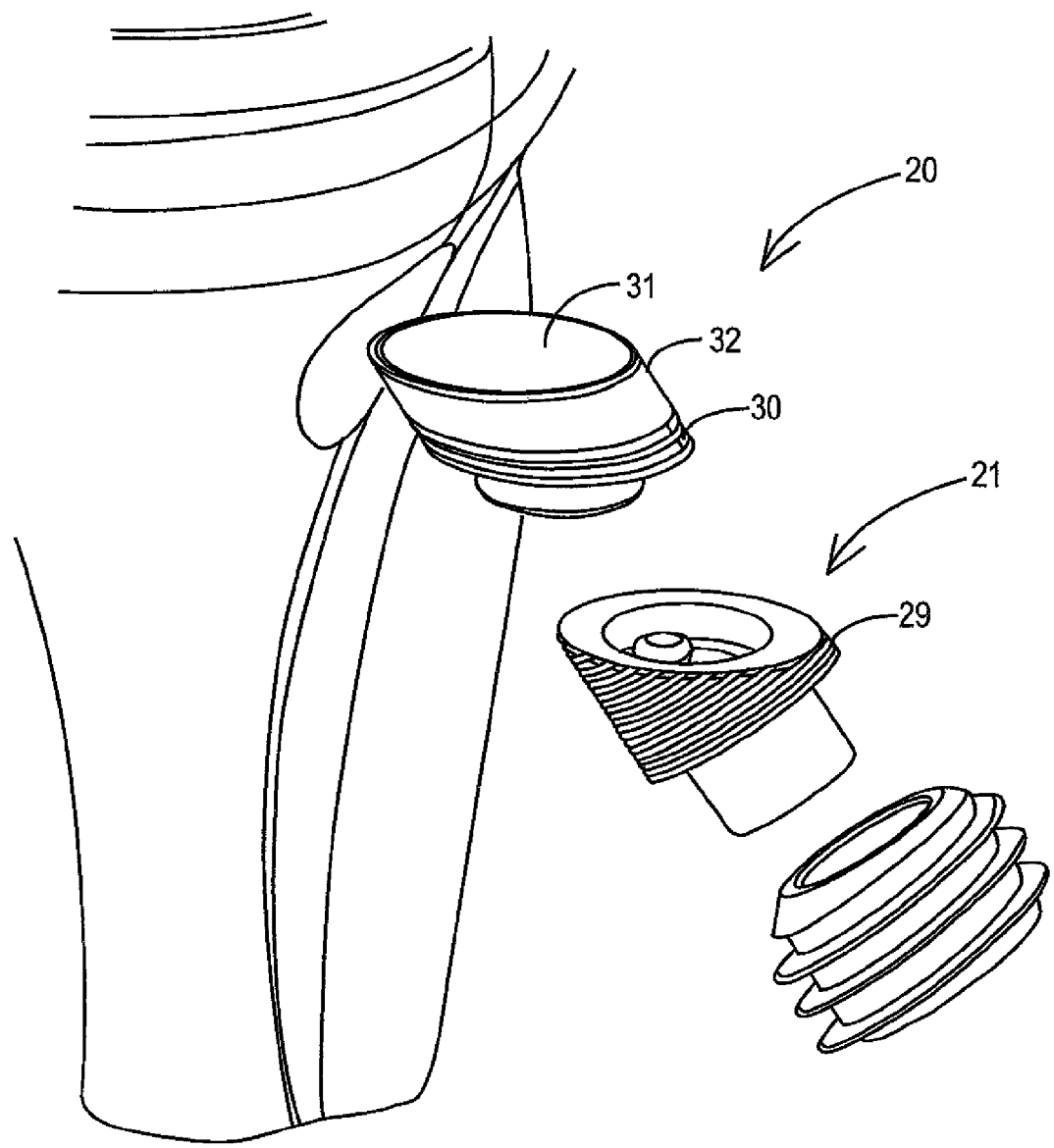
FIG. 9 is an exploded view of one exemplary implant according to the present invention.

FIG. 9 depicts another exploded view of the implant 130. The bearing surface component 20 may include grooves or rings 30 to aid in transferring mechanical loads to the surrounding bone, and may contain a contoured superior surface 31 to better match the existing articular surface. The intermediate mount 21 may also have similar load transferring features 29.

Figure 10:
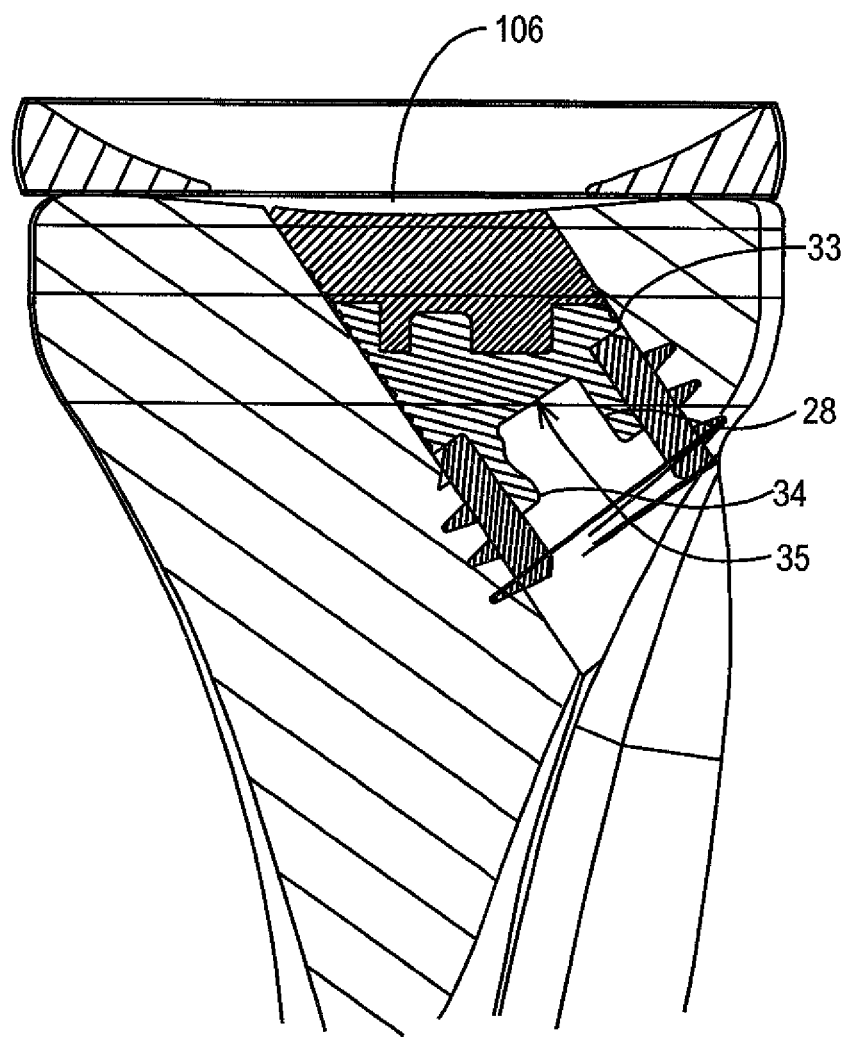
FIG. 10 is an in situ view of one exemplary implant according to the present invention.
Figure 11:
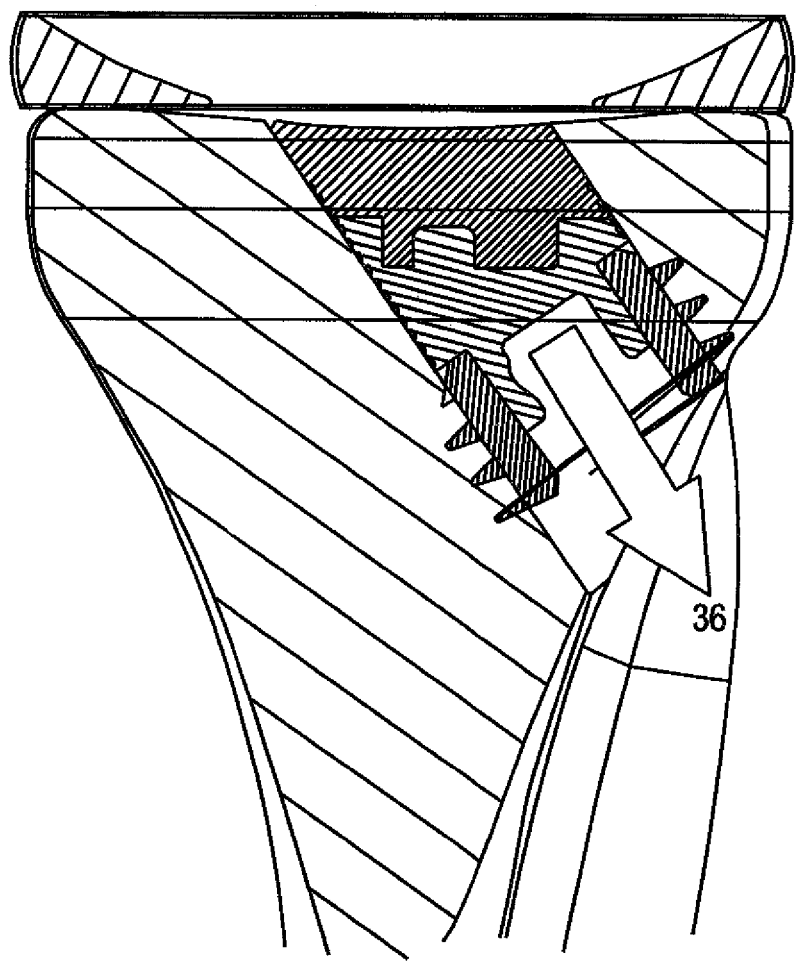
FIG. 11 is an in situ view of one exemplary implant according to the present invention.

FIG. 10 depicts the implant inserted into the bone. The proximal end of the mount component may include a bore 28 which allows for the insertion of a stand-off post 35 that works in conjunction with the hexdriver used for advancing the screw component. The stand-off permits the two components to remain slightly separated at the joint between the two devices 33 during the driving of the screw. This will allow for fine adjustment of the screw depth to bring the implant up to a position flush or slightly recessed to the existing articular surface 106 of the tibia. Using the stand-off post 35, engaged into the mount bore, the bearing surface and intermediate mount assembly can be rotated independently of the screw component to ensure it is properly aligned with respect to the tibial articular surface. Once all alignments are complete, a downward force 36 on the intermediate mount component will seat the tapers and lock all components into a fixed position, as depicted in FIG. 11.

Materials well known in the field of orthopedics can be used for the implant components. For example, UHMWPE for the bearing surface, and Titanium or Cobalt-Chromium Alloys used for the intermediate mount and fixation elements. However, as the most common cause for failure of such components is related to the wear debris of the UHMWPE, it the bearing surface component may be formed out of alternate materials which might provide clinical advantages based on their hydrophilic, low-friction characteristics. For example, recent developments in the fields of durable polyurethanes and structural hydrogels suggest that these materials, loaded into a suitable base, could be effective alternatives when rigidly fixed in bone.

Figure 12:
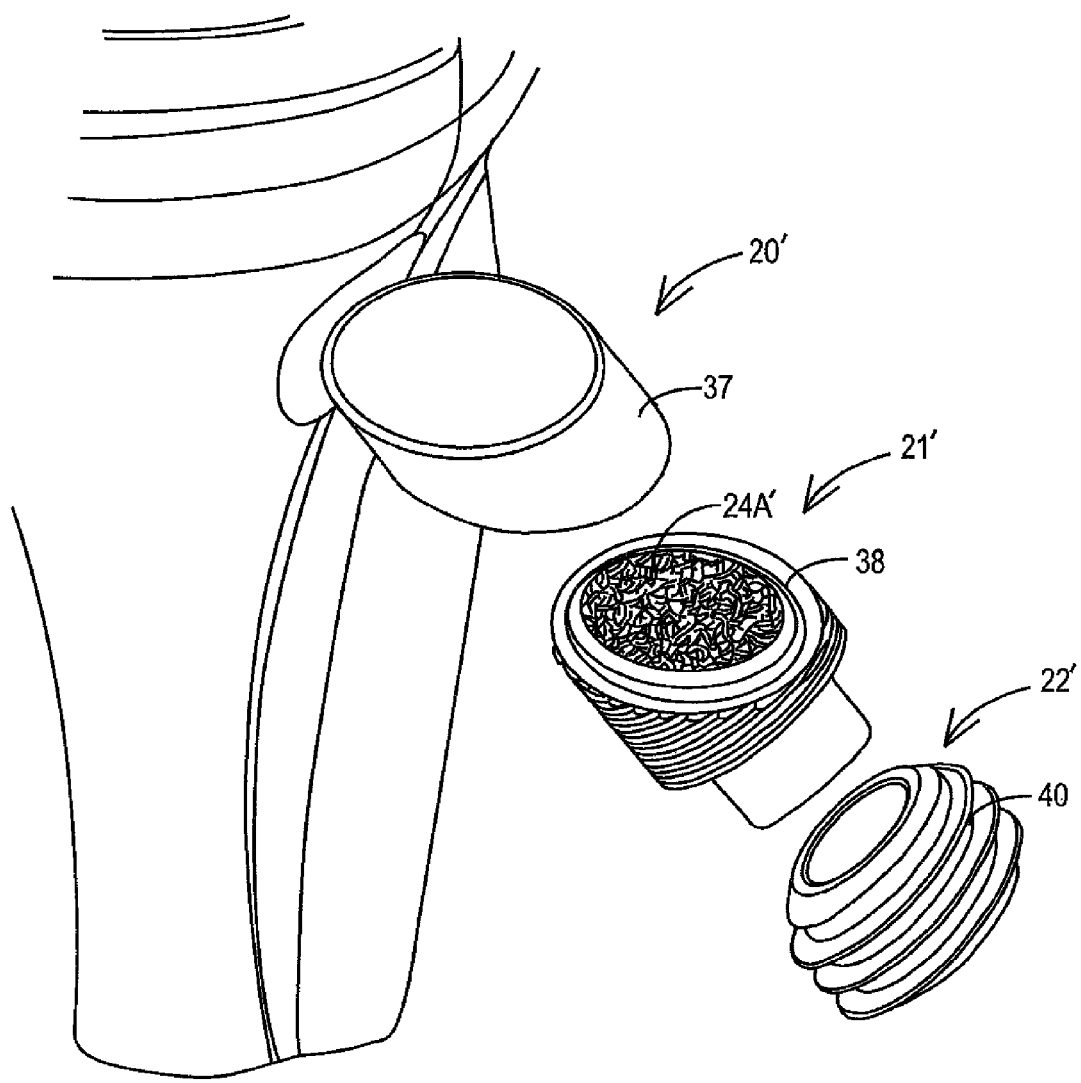
FIG. 12 is an exploded view of another exemplary implant according to the present invention.
Figure 13:
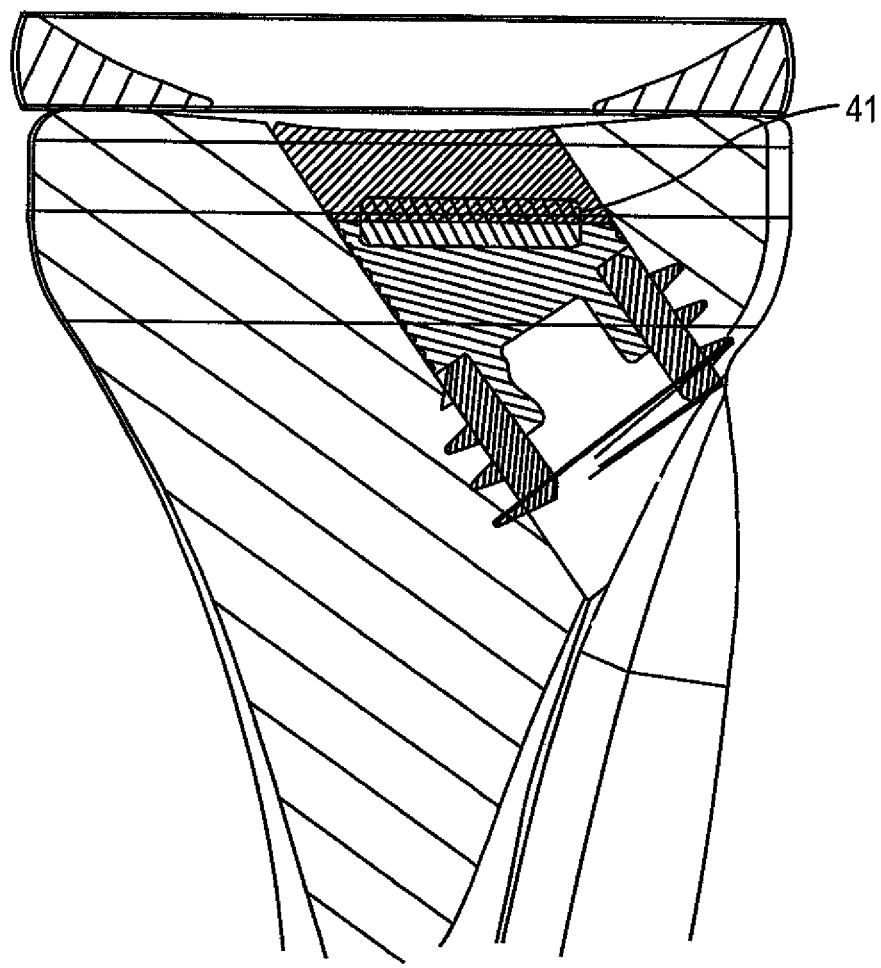
FIG. 13 is an in situ view of another exemplary implant according to the present invention.

FIG. 12 depicts an alternative exemplary embodiment of the implant of the present invention. In this embodiment, the intermediate mount 21' may include a wound and compressed wire portion 38 that may sintered into the bore 24A' in the intermediate mount. The wire portion 38 may be formed of a material similar to the material used for the intermediate mount. This may be advantageous if the wire portion and mount are heated to a temperature approaching the melting temperature for the materials, the components can fuse together to form a solid mass with controllable pore sizing to include a semi-continuous network of open spaces (i.e., porous material). The porous material may then be utilized as a base and a gel or elostomeric material may be cast into it. As shown in FIG. 13, this provides a mechanical interlock 41 between the cast material and the structural base.

Numerous alternatives will be recognized by those skilled in the art. For example, the angled bearing element can include fixation means attached thereon, so that the bearing element is screwed directly into bone. Alternatively, the fixation system could include an angled bearing element and a fixation element, without the need for an intermediate mount member. These and other alternatives will become apparent from the foregoing detailed description, and all such alternatives are deemed within the scope of the present invention, only as limited by the claims.

What is claimed is:

1. A surgical method comprising:
    positioning a targeting ring portion of a drill guide substantially on a superior tibial surface underneath a meniscus of a knee, said drill guide comprising an arm section having said targeting portion extending from a first portion of said arm section and a bore portion extending from a second portion of said arm section at angle relative to said arm section, said bore portion
    defining a passageway wherein a longitudinal axis of said passageway extends through at least a portion of said targeting ring portion;
    moving said bore portion against a portion of a distal tibia;
    inserting a cutting tool through said passageway of said bore portion;
    advancing said cutting tool through said tibia to said superior tibial surface to form an implant cavity on said superior tibial surface without removal of said meniscus; and
    securing a load bearing surface of a prosthetic proximate said superior tibial surface.

2. The method of claim 1, wherein advancing said cutting tool through said tibia to said superior tibial surface further comprises forming a tunnel having a first opening in said distal tibia and a second opening in said superior tibial surface.

3. The method of claim 2, further comprising inserting said prosthetic through said first opening.

4. The method of claim 3, further comprising securing a load bearing surface of said prosthetic proximate said second opening and said superior tibial surface.

\* \* \* \* \*